United States Patent
Sugihara

(10) Patent No.: US 10,487,344 B2
(45) Date of Patent: Nov. 26, 2019

(54) METHOD OF PRODUCING FATTY ACIDS OR LIPIDS BY USING ACYLTRANSFERASE

(71) Applicant: Kao Corporation, Chuo-ku, Tokyo (JP)

(72) Inventor: Shinji Sugihara, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/755,247

(22) PCT Filed: Sep. 1, 2016

(86) PCT No.: PCT/JP2016/075723
§ 371 (c)(1),
(2) Date: Feb. 26, 2018

(87) PCT Pub. No.: WO2017/043419
PCT Pub. Date: Mar. 16, 2017

(65) Prior Publication Data
US 2018/0245110 A1    Aug. 30, 2018

(30) Foreign Application Priority Data

Sep. 11, 2015   (JP) .................................. 2015-179167

(51) Int. Cl.
| | |
|---|---|
| *C12P 7/64* | (2006.01) |
| *C12N 9/16* | (2006.01) |
| *C12N 9/10* | (2006.01) |
| *C07K 14/405* | (2006.01) |
| *C12N 15/09* | (2006.01) |
| *C12N 15/82* | (2006.01) |

(52) U.S. Cl.
CPC .......... *C12P 7/6409* (2013.01); *C07K 14/405* (2013.01); *C12N 9/1025* (2013.01); *C12N 9/16* (2013.01); *C12N 15/09* (2013.01); *C12N 15/8247* (2013.01); *C12P 7/6436* (2013.01); *C12P 7/6445* (2013.01); *C12Y 301/02014* (2013.01)

(58) Field of Classification Search
None
See application file for complete search history.

(56) References Cited

U.S. PATENT DOCUMENTS

| | | |
|---|---|---|
| 2013/0197247 A1 | 8/2013 | Franklin et al. |
| 2013/0316410 A1 | 11/2013 | Franklin et al. |
| 2014/0162329 A1 | 6/2014 | Coppersmith et al. |
| 2015/0307860 A1 | 10/2015 | Ozakki et al. |

FOREIGN PATENT DOCUMENTS

| | | |
|---|---|---|
| JP | 2014-014334 A | 1/2014 |
| JP | 2017-209064 A | 11/2017 |
| WO | WO 95/27791 A1 | 10/1995 |
| WO | WO 00/60095 A2 | 10/2000 |
| WO | WO 2009/120366 A2 | 10/2009 |
| WO | WO 2011/156520 A2 | 12/2011 |
| WO | WO 2011/161093 A1 | 12/2011 |
| WO | WO 2017/203827 A1 | 11/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
International Search Report (ISR) for PCT/JP2016/075723; I.A. fd Sep. 1, 2016, dated Oct. 11, 2016 from the Japan Patent Office, Tokyo, Japan.
International Preliminary Report on Patentability (IPRP), Chapter I of the Patent Cooperation Treaty, including the Written Opinion for PCT/JP2016/075723; I.A. fd Sep. 1, 2016, dated Mar. 13, 2018, by the International Bureau of WIPO, Geneva, Switzerland.
Database DDBJ/EMBL/GenBank [online], Accession No. Q6MBK7 <http://www.ncbi.nlm.nih.gov/protein/Q6MBK7> Oct. 31, 2006 uploaded, [retrieved on Sep. 20, 2016] Horn, M. et al., Definition: Putative glycerol-3-phosphate acyltransferase.
Database DDBJ/EMBL/GenBank [online], Accession No. CCB91825 <http://www.ncbi.nlm.nih.gov/protein/337293838?sat=2&satkey=32065502> Jun. 22, 2011 uploaded, [retrieved on Sep. 20, 2016] Collingro, A. et al., Definition: glycerol-3-phosphate acyltransferase, chloroplastic [Waddlia chondrophila 2032/99].

* cited by examiner

Primary Examiner — Christian L Fronda
(74) *Attorney, Agent, or Firm* — Sterne, Kessler, Goldstein & Fox P.L.L.C.

(57) ABSTRACT

A method of producing lipids, containing the steps of:
culturing a transformant in which the expression of a gene encoding the following protein (A) or (B) is enhanced, and
producing fatty acids or lipids containing these fatty acids as components:
(A) a protein consisting of the amino acid sequence set forth in SEQ ID NO: 1; and
(B) a protein consisting of an amino acid sequence having 44% or more identity with the amino acid sequence of the protein (A), and having acyltransferase activity.

20 Claims, No Drawings
Specification includes a Sequence Listing.

SEQUENCE LISTING

<160> NUMBER OF SEQ ID NOS: 51

<210> SEQ ID NO 1
<211> LENGTH: 424
<212> TYPE: PRT
<213> ORGANISM: Nannochloropsis oculata

<400> SEQUENCE: 1

Met Ser Lys Ser Ser Phe Ile Cys Val Leu Ala Thr Ala Ala Ala Met
1               5                   10                  15

```
Leu Ala Ala Thr Thr Gln Ala Phe Val Leu Pro Thr Ser Arg Leu Leu
            20                  25                  30

Gly Thr Ser Ser Leu Lys Met Met Ala Ala Gly Thr Thr Gln Ala Gly
        35                  40                  45

Glu Lys Lys Ala Leu Thr Val Ala Asp Val Lys Thr Arg Leu Ile Glu
50                      55                  60

Lys Ile Thr Ser Asp Pro Asn Met Lys Leu Pro Asp Gln Phe Gln Gln
65                      70                  75                  80

Ala Leu Thr Asp Ile Leu Asp Gly Met Thr Glu Val Ala Glu Asn Thr
                85                  90                  95

Gly Leu Asp Pro Glu Lys Tyr Gln Glu Met Leu Gly Leu Leu Met Lys
                100                 105                 110

Glu Ala Ala Glu Asn Ser Arg Ser Leu Tyr Gln Phe Glu Pro Phe His
                115                 120                 125

Lys Asn Ile Arg Gly Pro Val Asp Phe Thr Ala Phe Gly Glu Asn Phe
            130                 135                 140

Phe Asp Ile Leu Cys Val Lys Glu Gln Ser Gly Val Leu Gly Arg Lys
145                 150                 155                 160

Asn Met Ala Lys Ile Val Asp Tyr Val Arg Gln Gly His Asn Val Val
                165                 170                 175

Leu Leu Ala Asn His Gln Thr Glu Pro Asp Pro Tyr Ile Leu Arg Ser
                180                 185                 190

Ala Phe Lys Arg Leu Val Pro Ala Asp Asp Pro Leu Leu Asp Arg Leu
            195                 200                 205

Val Phe Val Ala Gly Ala Lys Val Arg Thr Asp Leu Phe Thr Ile Pro
            210                 215                 220

Phe Ser Lys Gly Leu Asn Leu Ile Cys Ile His Ser Lys Lys Tyr Ile
225                 230                 235                 240

Glu Asp Asp Pro Ala Thr Lys Pro Leu Lys Thr Gln Glu Asn Leu Ala
                245                 250                 255

Ala Met Lys Ala Leu Gln Gly Leu Ile Val Glu Gly Gly His Ile Leu
                260                 265                 270

Trp Val Ala Pro Ser Gly Gly Arg Asp Arg Thr Asp Val His Thr Gly
            275                 280                 285

Lys Met Ala Val Ala Pro Phe Asp Ser Arg Ala Val Asp Met Phe Arg
290                 295                 300

Val Leu Ser Thr Lys Ser Gln His Pro Thr His Phe Phe Pro Leu Ser
305                 310                 315                 320

Met Leu Thr Ala Gln Val Leu Pro Pro Ala Lys Val Ala Met Glu
                325                 330                 335

Val Gly Glu Arg Arg Leu Val Ala Arg Arg Pro Val His Val Tyr Phe
            340                 345                 350

Gly Asp Glu Leu Thr Pro Glu Arg Val Gly Ser Glu Phe Val Ala Arg
            355                 360                 365

Lys Met Lys Asp Gly Thr Ala Glu Gly Leu Thr Glu Glu Leu Met
370                 375                 380

Lys Lys Ala Gly Lys Glu Gly Phe Thr Tyr Val Ala Glu Gly Asp Val
385                 390                 395                 400

Lys Arg His Tyr Asp Val Leu Met Gly Leu Asp Leu Val Leu Glu Glu
                405                 410                 415

Glu Glu Val Ser Val Gln Tyr His
            420
```

<210> SEQ ID NO 2
<211> LENGTH: 1275
<212> TYPE: DNA
<213> ORGANISM: Nannochloropsis oculata

<400> SEQUENCE: 2

| | | | | | |
|---|---|---|---|---|---|
| atgagcaagt | cctccttcat | atgtgtcctg | gctacggctg | cggccatgct | ggccgccacc | 60 |
| acccaggcgt | tgtcctccc | aaccagccgg | ctattgggga | catcgtcgtt | gaaaatgatg | 120 |
| gccgccggca | caacccaggc | aggcgagaaa | aaggccttga | ctgtggcgga | tgtgaagacg | 180 |
| aggctcatag | aaaagattac | ctccgacccg | aacatgaagc | tgcccgacca | gttccagcaa | 240 |
| gcgttgaccg | acattttgga | cggcatgact | gaagtggcag | aaaacacggg | cctggacccc | 300 |
| gagaagtacc | aagaaatgct | ggggttgctc | atgaaggagg | cagcagagaa | ctcccgtcc | 360 |
| ttgtatcagt | tcgagccgtt | ccacaaaaac | atccggggtc | ctgtggactt | cacggcattt | 420 |
| ggagaaaatt | tctttgacat | cctttgcgtc | aaggagcaaa | gcggagtctt | gggccggaag | 480 |
| aacatggcca | aaatcgtcga | ctacgtccga | caaggacaca | acgtggtgct | cctggccaac | 540 |
| catcagacgg | agcccgatcc | ctacatcctc | cggtcggcct | tcaagcgcct | ggtgccggcg | 600 |
| gatgatcctc | tgctggaccg | gctggtgttc | gtggctggcg | cgaaagtacg | cacggatttg | 660 |
| ttcaccatcc | ccttctccaa | gggactgaat | tgatatgca | tccactccaa | gaagtacatc | 720 |
| gaggacgacc | ccgccaccaa | gcccctcaag | acacaagaga | atctggctgc | catgaaggcc | 780 |
| ctgcaaggcc | tcatcgtcga | aggcggacac | attctctggg | ttgcgccctc | cggcggccga | 840 |
| gaccggacgg | acgttcacac | ggggaagatg | gccgtggctc | ccttcgactc | ccgcgcggtg | 900 |
| gatatgttcc | gggtcttgag | caccaagagc | cagcacccta | cccacttctt | tcccttgtcc | 960 |
| atgctgacgg | cgcaggtcct | tcccctcca | gccaaagtgg | ccatgaggt | gggtgaacgt | 1020 |
| cggctggtgg | cgcgccgacc | cgtgcatgtg | tattttgggg | atgagctaac | ccctgaacgg | 1080 |
| gtgggaagtg | aatttgtggc | acgaaagatg | aaggacggca | cggcggaagg | tttgacggag | 1140 |
| gaggagctga | tgaagaaggc | ggggaaggag | ggttttacct | atgtggcgga | ggggatgtc | 1200 |
| aagaggcatt | atgatgtgct | tatgggcctg | gatctggtgt | tggaggaaga | ggaggtgtct | 1260 |
| gtgcagtacc | attaa | | | | | 1275 |

<210> SEQ ID NO 3
<211> LENGTH: 795
<212> TYPE: DNA
<213> ORGANISM: Artificial Sequence
<220> FEATURE:
<223> OTHER INFORMATION: Neomycin resistance gene

<400> SEQUENCE: 3

| | | | | | |
|---|---|---|---|---|---|
| atgattgaac | aagatggatt | gcacgcaggt | tctccggccg | cttgggtgga | gaggctattc | 60 |
| ggctatgact | gggcacaaca | gacaatcggc | tgctctgatg | ccgccgtgtt | ccggctgtca | 120 |
| gcgcaggggc | gcccggttct | ttttgtcaag | accgacctgt | ccggtgccct | gaatgaactg | 180 |
| caggacgagg | cagcgcggct | atcgtggctg | gccacgacgg | gcgttccttg | cgcagctgtg | 240 |
| ctcgacgttg | gcactgaagc | gggaagggac | tggctgctat | tgggcgaagt | gccggggcag | 300 |
| gatctcctgt | catctcacct | tgctcctgcc | gagaaagtat | ccatcatggc | tgatgcaatg | 360 |
| cggcggctgc | atacgcttga | tccggctacc | tgcccattcg | accaccaagc | gaaacatcgc | 420 |
| atcgagcgag | cacgtactcg | gatggaagcc | ggtcttgtcg | atcaggatga | tctggacgaa | 480 |
| gagcatcagg | ggctcgcgcc | agccgaactg | ttcgccaggc | tcaaggcgcg | catgcccgac | 540 |

```
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acgtatcgc cgctcccgat tcgcagcgca tcgccttcta tcgccttctt    780
gacgagttct tctga                                                     795

<210> SEQ ID NO 4
<211> LENGTH: 490
<212> TYPE: DNA
<213> ORGANISM: Artificial Sequence
<220> FEATURE:
<223> OTHER INFORMATION: Tubulin promoter

<400> SEQUENCE: 4
actgcgcatg gattgaccga cggccggttg ccaacttttg gggtcggccc cccttttcta    60
gcccttgccc gtccagcaat taaaaattat caacggcata ccggcactgg aagcttcggg    120
tttacaattt tggcttgcct tcctaatact gtaccgcgga gaacgtatga tattacagaa    180
aaatgccttg cacagttagc gcaaagggaa aacgtttctc cgccattgta ctttttggaa    240
gagggaaagc gattgtaaaa tatggctctc cgctacgaga gtttgggctg ttgatacatg    300
tgaaaataag tgtggacgac tttgaatgac ttgatcaggc tgtttgcaca tataaccagc    360
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt                                                           490

<210> SEQ ID NO 5
<211> LENGTH: 35
<212> TYPE: DNA
<213> ORGANISM: Artificial Sequence
<220> FEATURE:
<223> OTHER INFORMATION: PCR primer No. 5

<400> SEQUENCE: 5
tcttttttgt gaagcatgat tgaacaagat ggatt                               35

<210> SEQ ID NO 6
<211> LENGTH: 35
<212> TYPE: DNA
<213> ORGANISM: Artificial Sequence
<220> FEATURE:
<223> OTHER INFORMATION: PCR primer No. 6

<400> SEQUENCE: 6
tttcccccat cccgatcaga agaactcgtc aagaa                               35

<210> SEQ ID NO 7
<211> LENGTH: 35
<212> TYPE: DNA
<213> ORGANISM: Artificial Sequence
<220> FEATURE:
<223> OTHER INFORMATION: PCR primer No. 7

<400> SEQUENCE: 7
cgagctcggt acccgactgc gcatggattg accga                               35

<210> SEQ ID NO 8
<211> LENGTH: 20
<212> TYPE: DNA
```

```
<213> ORGANISM: Artificial Sequence
<220> FEATURE:
<223> OTHER INFORMATION: PCR primer No. 8

<400> SEQUENCE: 8
atatcaagaa gctgtctttt                                               20

<210> SEQ ID NO 9
<211> LENGTH: 25
<212> TYPE: DNA
<213> ORGANISM: Artificial Sequence
<220> FEATURE:
<223> OTHER INFORMATION: PCR primer No. 9

<400> SEQUENCE: 9
tcgggatggg ggaaaaaaac ctctg                                         25

<210> SEQ ID NO 10
<211> LENGTH: 36
<212> TYPE: DNA
<213> ORGANISM: Artificial Sequence
<220> FEATURE:
<223> OTHER INFORMATION: PCR primer No. 10

<400> SEQUENCE: 10
actctagagg atcccctttc gtaaataaat cagctc                             36

<210> SEQ ID NO 11
<211> LENGTH: 1000
<212> TYPE: DNA
<213> ORGANISM: Nannochloropsis oculata

<400> SEQUENCE: 11
tcgggatggg ggaaaaaaac ctctgtgtgg gctgtcagtt gatactatta gaggtctttt    60
gttttgtttg tggctgcgtg tgtgtgtttg catgagaaat agacttgaga atatcggaag   120
gaactttgac atggtaaacg aggaaaagaa aatcttcaaa aaggaataat gggtaaaaac   180
aaggagcacc gggtctcttt agaaatgctt ctcggcggaa aaccagaaaa aaaggtagaa   240
tatgtcgact ttttcgctta tcattataga atgaaagatc gaatggccaa gggatttata   300
aattctttct ttatgttgtc gtagaactta cttttccatcc cgagggaggt gtatgcaggc   360
caaaccctct gacatgggcg caatatctct atgaaaggtt gttggaatac attgtccgac   420
ctccttcgag gcggagccgc atagttgaag tataggtgct tgcttcatcc atctcatgac   480
gctttgccag tgactcactc atgcatgtga cacatttagt tctgctcgct caagcctggc   540
ccctcctgac atgcacacat tgcacttgta ggtgggccac gtttagtata gacgccaccc   600
ctgtcgcacc atcggtccca gagcaggagc acgcttccct actcctgtac gctcccctg   660 cttccccccc tgctcgtcaa cgatggcgac gccagcggct gcgaattaca gtgacggcgc   720
ggccgctcag gatgacagct cctctccttc aacatctccc aatcttccac ccccgcccat   780
gtcgtcgttc gtacggccta tgctgaccga tatgtaccaa attacaatgg tcttcgcgta   840
ctggaagcaa aagcggcacc aggacagggc catctttgag ctcttttttcc ggaagacacc   900 ctttaaggga gagtttgcca ttatggccgg cattgacgaa gtactcaagt acttggccca   960
ctttcgcttc tccgaggagg agctgattta tttacgaaag                        1000

<210> SEQ ID NO 12
<211> LENGTH: 35
<212> TYPE: DNA
<213> ORGANISM: Artificial Sequence
```

```
<220> FEATURE:
<223> OTHER INFORMATION: PCR primer No. 12

<400> SEQUENCE: 12
gggatcctct agagtcgacc tgcaggcatg caagc                                35

<210> SEQ ID NO 13
<211> LENGTH: 20
<212> TYPE: DNA
<213> ORGANISM: Artificial Sequence
<220> FEATURE:
<223> OTHER INFORMATION: PCR primer No. 13

<400> SEQUENCE: 13
cgggtaccga gctcgaattc                                                 20

<210> SEQ ID NO 14
<211> LENGTH: 35
<212> TYPE: DNA
<213> ORGANISM: Artificial Sequence
<220> FEATURE:
<223> OTHER INFORMATION: PCR primer No. 14

<400> SEQUENCE: 14
cagcccgcat caacaatgag caagtcctcc ttcat                                35

<210> SEQ ID NO 15
<211> LENGTH: 35
<212> TYPE: DNA
<213> ORGANISM: Artificial Sequence
<220> FEATURE:
<223> OTHER INFORMATION: PCR primer No. 15

<400> SEQUENCE: 15
ctcttccaca gaagcttaat ggtactgcac agaca                                35

<210> SEQ ID NO 16
<211> LENGTH: 35
<212> TYPE: DNA
<213> ORGANISM: Artificial Sequence
<220> FEATURE:
<223> OTHER INFORMATION: PCR primer No. 16

<400> SEQUENCE: 16
cgagctcggt acccgttctt ccgcttgttg ctgcc                                35

<210> SEQ ID NO 17
<211> LENGTH: 25
<212> TYPE: DNA
<213> ORGANISM: Artificial Sequence
<220> FEATURE:
<223> OTHER INFORMATION: PCR primer No. 17

<400> SEQUENCE: 17
tgttgatgcg ggctgagatt ggtgg                                           25

<210> SEQ ID NO 18
<211> LENGTH: 800
<212> TYPE: DNA
<213> ORGANISM: Nannochloropsis oculata

<400> SEQUENCE: 18
ttcttccgct tgttgctgcc gatggcggcc atggtctcta agatggagtg gatggaggag     60
gaggcgagcg tagcagcaag cgtgagttat acagccaggc acatgtcgca atccttcggt    120
```

| | |
|---|---|
| ctcgggctta aaatccacgc actaatcacg ctgggccatg caaagagcaa tgccgaggcc | 180 |
| caccacacaa aacgctgtgt cgcgcgttgc ggcctgaagc ttcatacttc ttagtcgccg | 240 |
| ccaaaagggc tcgagagacg agacccgttg gcatgaccga tgttgttcga cgcggtttgc | 300 |
| ttcgtcacag tcgacgtgat tcaggaatct ggagcctgca gatcattttt ttcagcctga | 360 |
| tatcgttctt ttccactgag aaccatcaga ccaccttttc ttccattgtg tgaaggagta | 420 |
| ggagttgccg tgctgctttg tgggagacat ctgcgatggt gaccagcctc ccgtcgtctg | 480 |
| gtcgacgtga cgagcctctt cactgttctt cgacggagag acgcaagcga gacggctcta | 540 |
| gaccttttgg acacgcattc tgtgtgtgaa ctagtggaca gtgataccac gtctgaaagc | 600 |
| tcaccactgc ccatggtgca gctacttgtc acaaagtttt gactccgtcg gtatcaccat | 660 |
| tcgcgctcgt gtgcctggtt gttccgccac gccggcctgc cccggggcgg ggcaatattc | 720 |
| taaaatctca cgcaaaacac cgcacttacc cctcacacat attcgtgata gaccaccacc | 780 |
| aatctcagcc cgcatcaaca | 800 |

<210> SEQ ID NO 19
<211> LENGTH: 643
<212> TYPE: DNA
<213> ORGANISM: Artificial Sequence
<220> FEATURE:
<223> OTHER INFORMATION: VCP1 terminator

<400> SEQUENCE: 19

| | |
|---|---|
| gcttctgtgg aagagccagt ggtagtagca gtagcagcag cagtagcagc cgcagcactc | 60 |
| agtgttggcg cgagagattg tccatccctt cttaacctac cggaagagaa ataaggcctt | 120 |
| tctcccgtag ctgtcttcgt ttgtttgtgc tgattgcttg atatgagagt gttgaattcc | 180 |
| tgcatcatgt ttttctctgt agtccttttcc taccccgtc atttctttt ctccctggtt | 240 |
| cttcttttgt caccttatt ttacataaaa ttttctttgt ttatagtgag aggaaggtag | 300 |
| agaggggaaa acaagaacaa cgaacgcaag cgtgtgaaag gagggcgagt agaagagaaa | 360 |
| cagatctgtt gagcattgag agtggagccg ggggaaaggc ttgtgtgttg tctttgaaaa | 420 |
| agttgtttaa atcacgaatc cgttagttct catgtgtacc tctttcacta catgtgatgg | 480 |
| agaaaacaaa agtgtgagga ttaattgaag aaaaagaaga gttcgacacg tcaaaccgcc | 540 |
| caaaagacgt cacaaagaga acttgattct ctttgccgtg ttgatcctgt cttttccccc | 600 |
| agcttttctt gccacccgtg gcacacgaga tggacaagat cag | 643 |

<210> SEQ ID NO 20
<211> LENGTH: 21
<212> TYPE: DNA
<213> ORGANISM: Artificial Sequence
<220> FEATURE:
<223> OTHER INFORMATION: PCR primer No. 20

<400> SEQUENCE: 20

| | |
|---|---|
| gcttctgtgg aagagccagt g | 21 |

<210> SEQ ID NO 21
<211> LENGTH: 35
<212> TYPE: DNA
<213> ORGANISM: Artificial Sequence
<220> FEATURE:
<223> OTHER INFORMATION: PCR primer No. 21

<400> SEQUENCE: 21

| | |
|---|---|
| caatccatgc gcagtctgat cttgtccatc tcgtg | 35 |

<210> SEQ ID NO 22
<211> LENGTH: 20
<212> TYPE: DNA
<213> ORGANISM: Artificial Sequence
<220> FEATURE:
<223> OTHER INFORMATION: PCR primer No. 22

<400> SEQUENCE: 22
actgcgcatg gattgaccga                                              20

<210> SEQ ID NO 23
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 23
atggccaagc tgaccagcgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg gacgcctcc gggccggcca tgaccgagat cggcgagcag     300
ccgtgggggc gggagttcgc cctgcgcgac ccggccggca actgcgtgca cttcgtggcc     360
gaggagcagg actaa                                                   375

<210> SEQ ID NO 24
<211> LENGTH: 32
<212> TYPE: DNA
<213> ORGANISM: Artificial Sequence
<220> FEATURE:
<223> OTHER INFORMATION: PCR primer No. 24

<400> SEQUENCE: 24
tccgagcaga ttatggccaa gctgaccagc gc                                 32

<210> SEQ ID NO 25
<211> LENGTH: 36
<212> TYPE: DNA
<213> ORGANISM: Artificial Sequence
<220> FEATURE:
<223> OTHER INFORMATION: PCR primer No. 25

<400> SEQUENCE: 25
tttcccccat cccgattagt cctgctcctc ggccac                             36

<210> SEQ ID NO 26
<211> LENGTH: 38
<212> TYPE: DNA
<213> ORGANISM: Artificial Sequence
<220> FEATURE:
<223> OTHER INFORMATION: PCR primer No. 26

<400> SEQUENCE: 26
gcggccgctc tagagtgcga gacggcccac gccgggac                           38

<210> SEQ ID NO 27
<211> LENGTH: 39
<212> TYPE: DNA
<213> ORGANISM: Artificial Sequence
<220> FEATURE:

<223> OTHER INFORMATION: PCR primer No. 27

<400> SEQUENCE: 27
acaaaatatt aacgcctagc taatatcaat tttctttgg          39

<210> SEQ ID NO 28
<211> LENGTH: 287
<212> TYPE: PRT
<213> ORGANISM: Nannochloropsis oculata

<400> SEQUENCE: 28

```
Met Thr Pro Leu Ala Phe Thr Val Leu Gly Lys Leu Gly Gly Thr Leu
1               5                   10                  15

Thr Phe Ala Cys Val Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285
```

<210> SEQ ID NO 29
<211> LENGTH: 864
<212> TYPE: DNA
<213> ORGANISM: Nannochloropsis oculata

<400> SEQUENCE: 29
atgacgcctt tggccttcac ggtgctcggc aagcttggtg gcacgttgac ttttgcttgt    60
gtacgacgga ggcttttatca cttgttacgg cgggcaactt tgtcctccca ttatcaggtc   120

```
actcggcctt acggtcacag caattccggc tgttcacata gcactaccac acttagaacc    180
agcttcccag tcctctttgc gcaattggca gcagccactg ctgccgtcgt cgctgccatt    240
tccctgccgt cgcctagtct atgcgagacg gcccacgccg ggactgagga gagacgaggt    300
gagaggaagg caatgaggga ggatggtgga aaaggcgagg ccacctcgtc tgctacatgc    360
aatccatcct tattcgaaca tcatgatcgc gtcgacacca agctgcatcg ggcctatcct    420
gaattcctga agttccacct tatccacgag acgctccgag gcaaagagaa aattgatggc    480
tacgaagttt acaaagacag gcgggatgat tcaattgtgg cgtatgctcg ccttggcaaa    540
ctgctgagcg acaccccga cataatccac ggagggtcca ttgcggcttt gctggacaat    600
accatgggag ttgcctttt cgccgccaag cgtggcaatg gttttacagc aaatctcacc    660
atcaactaca agcgacccat cacgtgtggc accgaagtca agttttagc tcgagtagag    720 aaggtggaag ggcgcaaggt cttcttgcgg gccgagattc gagacgctaa ggatgaggct    780
atcctctaca ctgaagccaa atccctcttc atcacgtctc aaagtccttt attgaagggc    840
ccaaagaaaa ttgatattag ctag                                          864

<210> SEQ ID NO 30
<211> LENGTH: 20
<212> TYPE: DNA
<213> ORGANISM: Artificial Sequence
<220> FEATURE:
<223> OTHER INFORMATION: PCR primer No. 30

<400> SEQUENCE: 30
ctctagagcg gccgccaccg                                                20

<210> SEQ ID NO 31
<211> LENGTH: 24
<212> TYPE: DNA
<213> ORGANISM: Artificial Sequence
<220> FEATURE:
<223> OTHER INFORMATION: PCR primer No. 31

<400> SEQUENCE: 31
gcgttaatat tttgttaaaa ttcg                                           24

<210> SEQ ID NO 32
<211> LENGTH: 39
<212> TYPE: DNA
<213> ORGANISM: Artificial Sequence
<220> FEATURE:
<223> OTHER INFORMATION: PCR primer No. 32

<400> SEQUENCE: 32
ctggacaata ccatgggatg ggccttttc gccgccaag                            39

<210> SEQ ID NO 33
<211> LENGTH: 20
<212> TYPE: DNA
<213> ORGANISM: Artificial Sequence
<220> FEATURE:
<223> OTHER INFORMATION: PCR primer No. 33

<400> SEQUENCE: 33
catggtattg tccagcaaag                                                20

<210> SEQ ID NO 34
<211> LENGTH: 603
<212> TYPE: DNA
```

<213> ORGANISM: Nannochloropsis oculata

<400> SEQUENCE: 34

```
tgcgagacgg cccacgccgg gactgaggag agacgaggtg agaggaaggc aatgagggag    60
gatggtggaa aaggcgaggc cacctcgtct gctacatgca atccatcctt attcgaacat   120
catgatcgcg tcgacaccaa gctgcatcgg gcctatcctg aattcctgaa gttccacctt   180
atccacgaga cgctccgagg caaagagaaa attgatggct acgaagttta caaagacagg   240
cgggatgatt caattgtggc gtatgctcgc cttggcaaac tgctgagcgg acaccccgac   300
ataatccacg agggtccat tgcggctttg ctggacaata ccatgggatg ggccttttc    360
gccgccaagc gtggcaatgg ttttacagca aatctcacca tcaactacaa gcgacccatc   420
acgtgtggca ccgaagtcaa agttttagct cgagtagaga aggtggaagg cgcaaggtc    480
ttcttgcggg ccgagattcg agacgctaag gatgaggcta tcctctacac tgaagccaaa   540
tccctcttca tcacgtctca aagtccttta ttgaagggcc caaagaaaat tgatattagc   600
tag                                                                  603
```

<210> SEQ ID NO 35
<211> LENGTH: 802
<212> TYPE: DNA
<213> ORGANISM: Artificial Sequence
<220> FEATURE:
<223> OTHER INFORMATION: VCP1 promoter

<400> SEQUENCE: 35

```
ggcggtctt tgtcctttcc tctatagccc gcccgtctag agggcacacg cgatgatctt    60
tatatctctt catgtgtctt tgttttaact aggatactgc cgggtgaatg cccatcggac   120
aagaggccaa actctatcta cacccttttg acttctgttg tggtcgtagt gtgtgcttgc   180
atgccctgaa agtccaggca tcccacttgt gctctaaccc cattcaaaac agcagaagtg   240
cttaattaag atatagattc atgatctcct gtccccctcct tcttaccttt tcacaaacct   300
cacacagaag tctccactct tcgcctctaa aacctctttt taaattatgg taagttcgtg   360
cggcagtggg ttttcggatc tatatttgtc aagatccagt tcaaggtcag ggatgtagat   420
taagtacaga aggagaagca caagcgcgcc agttcgcccc tcacggcctg gagcagggca   480
tttaatccct ctatcttacc agaaccatac tatacaacca atcctgttgg catcgctctg   540
tctatttgtc gtgcgtgcat gtgtccatgg tgtggtgggg ggcaggggtt ttcggggttg   600
cggttgaagg caccttatca gaaagatgcc ctcagagata gaggtagccc cctcccccg    660
atcttcgacc agtcctgtca ggcgaacact ttcacccgtc gttcacctcg ttacacacaa   720
ggagtagacc tctgaagttc taattgtcat aaatgcccct ccccccctccc tctttccctt   780
gatcctcccc tccgagcaga tt                                            802
```

<210> SEQ ID NO 36
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 36

```
atgaagaccg ccgctctcct cactgtctcc accctcatgg gcgcccaggc ctttatggcc    60
cccgccccca agttctcccg cacccgcggt gttgcgcgc                           99
```

<210> SEQ ID NO 37
<211> LENGTH: 37
<212> TYPE: DNA
<213> ORGANISM: Artificial Sequence
<220> FEATURE:
<223> OTHER INFORMATION: PCR primer No. 37

<400> SEQUENCE: 37
cgagctcggt acccgggcgg tcttttgtcc tttcctc                     37

<210> SEQ ID NO 38
<211> LENGTH: 22
<212> TYPE: DNA
<213> ORGANISM: Artificial Sequence
<220> FEATURE:
<223> OTHER INFORMATION: PCR primer No. 38

<400> SEQUENCE: 38
aatctgctcg gagggagga tc                                      22

<210> SEQ ID NO 39
<211> LENGTH: 36
<212> TYPE: DNA
<213> ORGANISM: Artificial Sequence
<220> FEATURE:
<223> OTHER INFORMATION: PCR primer No. 39

<400> SEQUENCE: 39
ccctccgagc agattatgaa gaccgccgct ctcctc                      36

<210> SEQ ID NO 40
<211> LENGTH: 28
<212> TYPE: DNA
<213> ORGANISM: Artificial Sequence
<220> FEATURE:
<223> OTHER INFORMATION: PCR primer No. 40

<400> SEQUENCE: 40
gcgcgcaaca ccgcgggtgc gggagaac                               28

<210> SEQ ID NO 41
<211> LENGTH: 1500
<212> TYPE: DNA
<213> ORGANISM: Nannochloropsis oculata

<400> SEQUENCE: 41
cagaaggagc cctcaaccta catgatgaag tgtgaaggac gaagaaagac gggaaagatt     60
aaaggctgag tgctacagta catctccagc tacgtcatat tttacacgct ctctctcccc    120
ctccctccct ccttccctcc ctccctccct cctcccccac ctcggggtcc cagctcgtac    180
tcatgatcga atacgaaatg cctgccaagg ccgccaggaa gggcacctgc gtcgagaagg    240
ccacaaaagc gggtggcacg tcgatctccg tattcttggc caggtacaga agaagccaa     300 acagtgctat gccacccaac acaggcacga acgtgaaggg taacagcctc ttgagcatcc    360
gattgcttat ctgctcgggc aagttaccca caatgccctc atccagcaga cgttgagttt    420
ctttgtactc ggcgatttcc cgcatgtcca tctctcgttc catttccgct tggatttccc    480
agtaggacct tttttgacgc gcgctcagtc tgtctagctc gtctaggaa gcttgagagg     540 cagcgagggg gttgtcaggc tcgtttgctt ctgaagagga ggagggggg gaagaggagg    600 gaagggagga cgacggggct gcttttttgg gttgcttctt ggcgaagcct ttggggtgg    660 gtggttggtc cttgttgtcg tcagcggcgg cacggaaggg taggaaaggg gggtgtagag    720

```
gtgagaacga cggggatgcg gtggaggaat gtcttctgct ttgcaggata gaagaagggg    780
ggaagaagga ggaggagaaa ggcaaggtgg ggaggagaaa ggcggttatg aaggagggga    840
gaaggacgag gatgaggagg attgggacaa gaatggctgg cggccctctt gagctggcgg    900
ctggcatggt ttagaagggg cctggtttat gctggctcag tcctaagttg atgatgaaga    960
tgggaaagaa cggaggggggg gagtatgagt gagtcaatac atgcgaatga tacaggggca   1020
ggaggtcaag tatggcgctc tcagaaccta tgcgggttcc aatttatcat caggccaaag   1080
cacgcgccct gaggtttgtc tcacacaagt gagtccagaa tattttctgt gatatggcgg   1140
catcacttca gcatcagcta taacgccatc gcgaggatgc acgaacccgc gggaaacgcg   1200
gcaggactct gcgtcccggg atctcacatc gccgttgtgt gcgtgatcat cagatcgtgt   1260
gacgacggca cgaaggacaa gcaggcgatt taccaaagca aaaaagcgcg ctggtgttta   1320
gggcttggta gtacgattgg gatgatcagg gagagacttc ggcggagcaa gcattcatac   1380
agcttttttg agccatcctt gatcgcaacc tgccagatgc actcattcct ctttcgcatc   1440
accctcccta tccccacca ctccacattt cgcacacttc acgtgcacag ggagagagag   1500
```

<210> SEQ ID NO 42
<211> LENGTH: 382
<212> TYPE: PRT
<213> ORGANISM: Umbellularia californica

<400> SEQUENCE: 42

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240
```

Gly Pro Ala Phe Ile Asp Asn Val Ala Val Lys Asp Glu Ile Lys
                245                 250                 255

Lys Leu Gln Lys Leu Asn Asp Ser Thr Ala Asp Tyr Ile Gln Gly Gly
        260                 265                 270

Leu Thr Pro Arg Trp Asn Asp Leu Asp Val Asn Gln His Val Asn Asn
    275                 280                 285

Leu Lys Tyr Val Ala Trp Val Phe Glu Thr Val Pro Asp Ser Ile Phe
290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380

<210> SEQ ID NO 43
<211> LENGTH: 1149
<212> TYPE: DNA
<213> ORGANISM: Umbellularia californica

<400> SEQUENCE: 43
atggccacca cctctttagc ttccgctttc tgctcgatga aagctgtaat gttggctcgt        60
gatggccggg gcatgaaacc caggagcagt gatttgcagc tgagggcggg aaatgcgcca       120
acctctttga agatgatcaa tgggaccaag ttcagttaca cggagagctt gaaaaggttg       180
cctgactgga gcatgctctt tgcagtgatc acaaccatct tttcggctgc tgagaagcag       240
tggaccaatc tagagtggaa gccgaagccg aagctacccc agttgcttga tgaccatttt       300
ggactgcatg gttagttttt caggcgcacc tttgccatca gatcttatga ggtgggacct       360
gaccgctcca catctatact ggctgttatg aatcacatgc aggaggctac acttaatcat       420
gcgaagagtg tgggaattct aggagatgga ttcgggacga cgctagagat gagtaagaga       480
gatctgatgt gggttgtgag acgcacgcat gttgctgtgg aacggtaccc tacttggggt       540
gatactgtag aagtagagtg ctggattggt gcatctggaa ataatggcat gcgacgtgat       600
ttccttgtcc gggactgcaa aacaggcgaa attcttacaa gatgtaccag cctttcggtg       660
ctgatgaata caaggacaag gaggttgtcc acaatccctg acgaagttag aggggagata       720
gggcctgcat tcattgataa tgtggctgtc aaggacgatg aaattaagaa actacagaag       780
ctcaatgaca gcactgcaga ttacatccaa ggaggtttga ctcctcgatg gaatgatttg       840
gatgtcaatc agcatgtgaa caacctcaaa tacgttgcct gggttttga gaccgtccca       900 gactccatct ttgagagtca tcatatttcc agcttcactc ttgaatacag agagagtgc        960 acgagggata gcgtgctgcg gtccctgacc actgtctctg gtggctcgtc ggaggctggg      1020
ttagtgtgcg atcacttgct ccagcttgaa ggtgggtctg aggtattgag ggcaagaaca      1080
gagtggaggc ctaagcttac cgatagtttc agagggatta gtgtgatacc cgcagaaccg      1140
agggtgtaa                                                              1149

<210> SEQ ID NO 44
<211> LENGTH: 303
<212> TYPE: PRT

<213> ORGANISM: Cocos nucifera

<400> SEQUENCE: 44

| | | | | | | | | | | | | | | |
|---|---|---|---|---|---|---|---|---|---|---|---|---|---|---|
| Leu | Asp | Ser | Lys | Lys | Arg | Gly | Ala | Asp | Ala | Val | Ala | Asp | Ala | Ser | Gly |
| 1 | | | | 5 | | | | | 10 | | | | | 15 | |

| Val | Gly | Lys | Met | Val | Lys | Asn | Gly | Leu | Val | Tyr | Arg | Gln | Asn | Phe | Ser |
| | | | 20 | | | | | 25 | | | | | 30 | | |

| Ile | Arg | Ser | Tyr | Glu | Ile | Gly | Val | Asp | Lys | Arg | Ala | Ser | Val | Glu | Ala |
| | | 35 | | | | | 40 | | | | | 45 | | | |

| Leu | Met | Asn | His | Phe | Gln | Glu | Thr | Ser | Leu | Asn | His | Cys | Lys | Cys | Ile |
| 50 | | | | | 55 | | | | | 60 | | | | | |

| Gly | Leu | Met | His | Gly | Gly | Phe | Gly | Cys | Thr | Pro | Glu | Met | Thr | Arg | Arg |
| 65 | | | | 70 | | | | | 75 | | | | | 80 | |

| Asn | Leu | Ile | Trp | Val | Val | Ala | Lys | Met | Leu | Val | His | Val | Glu | Arg | Tyr |
| | | | 85 | | | | | 90 | | | | | 95 | | |

| Pro | Trp | Trp | Gly | Asp | Val | Val | Gln | Ile | Asn | Thr | Trp | Ile | Ser | Ser | Ser |
| | | | 100 | | | | | 105 | | | | | 110 | | |

| Gly | Lys | Asn | Gly | Met | Gly | Arg | Asp | Trp | His | Val | His | Asp | Cys | Gln | Thr |
| | | 115 | | | | | 120 | | | | | 125 | | | |

| Gly | Leu | Pro | Ile | Met | Arg | Gly | Thr | Ser | Val | Trp | Val | Met | Met | Asp | Lys |
| | 130 | | | | | 135 | | | | | 140 | | | | |

| His | Thr | Arg | Arg | Leu | Ser | Lys | Leu | Pro | Glu | Glu | Val | Arg | Ala | Glu | Ile |
| 145 | | | | | 150 | | | | | 155 | | | | | 160 |

| Thr | Pro | Phe | Phe | Ser | Glu | Arg | Asp | Ala | Val | Leu | Asp | Asp | Asn | Gly | Arg |
| | | | 165 | | | | | 170 | | | | | 175 | | |

| Lys | Leu | Pro | Lys | Phe | Asp | Asp | Ser | Ala | Ala | His | Val | Arg | Arg | Gly |
| | | 180 | | | | | 185 | | | | | 190 | | | |

| Leu | Thr | Pro | Arg | Trp | His | Asp | Phe | Asp | Val | Asn | Gln | His | Val | Asn | Asn |
| | | 195 | | | | | 200 | | | | | 205 | | | |

| Val | Lys | Tyr | Val | Gly | Trp | Ile | Leu | Glu | Ser | Val | Pro | Val | Trp | Met | Leu |
| | 210 | | | | | 215 | | | | | 220 | | | | |

| Asp | Gly | Tyr | Glu | Val | Ala | Thr | Met | Ser | Leu | Glu | Tyr | Arg | Arg | Glu | Cys |
| 225 | | | | | 230 | | | | | 235 | | | | | 240 |

| Arg | Met | Asp | Ser | Val | Val | Gln | Ser | Leu | Thr | Ala | Val | Ser | Ser | Asp | His |
| | | | 245 | | | | | 250 | | | | | 255 | | |

| Ala | Asp | Gly | Ser | Pro | Ile | Val | Cys | Gln | His | Leu | Leu | Arg | Leu | Glu | Asp |
| | | | 260 | | | | | 265 | | | | | 270 | | |

| Gly | Thr | Glu | Ile | Val | Arg | Gly | Gln | Thr | Glu | Trp | Arg | Pro | Lys | Gln | Gln |
| | | 275 | | | | | 280 | | | | | 285 | | | |

| Ala | Cys | Asp | Leu | Gly | Asn | Met | Gly | Leu | His | Pro | Thr | Glu | Ser | Lys |
| | 290 | | | | | 295 | | | | | 300 | | | | |

<210> SEQ ID NO 45
<211> LENGTH: 912
<212> TYPE: DNA
<213> ORGANISM: Cocos nucifera

<400> SEQUENCE: 45

```
ctcgattcca agaagagggg ggccgacgcg gtcgcagatg cctctggggt cggaagatg      60
gtcaagaatg gacttgttta caggcagaat ttttctatcc ggtcctacga aatcggggtt    120
gataaacgtg cttcggtaga ggcattgatg aatcatttcc aggaaacgtc gcttaaccat    180
tgcaagtgta ttggccttat gcatggcggc tttggttgta caccagagat gactcgaaga    240
aatctgatat gggttgttgc caaaatgctg gttcatgtcg aacgttatcc ttggtgggga    300
```

-continued

```
gacgtggttc aaataaatac gtggattagt tcatctggaa agaatggtat gggacgtgat    360
tggcatgttc atgactgcca aactggccta cctattatga ggggtaccag tgtctgggtc    420
atgatggata acacacgag gagactgtct aaacttcctg aagaagttag agcagagata    480 accccttct tttcagagcg tgatgctgtt tggacgata acggcagaaa acttcccaag    540
ttcgatgatg attctgcagc tcatgttcga aggggcttga ctcctcgttg gcatgatttc    600
gatgtaaatc agcatgtgaa caatgtcaaa tacgtcggct ggattcttga gagcgttcct    660
gtgtggatgt tggatggcta cgaggttgca accatgagtc tggaataccg gagggagtgt    720
aggatggata gtgtggtgca gtctctcacc gccgtctctt ccgaccacgc cgacggctcc    780
cccatcgtgt gccagcatct tctgcggctc gaggatggga ctgagattgt gaggggtcaa    840
acagaatgga ggcctaagca gcaggcttgt gatcttggga acatgggtct gcacccaact    900
gagagtaaat ga                                                         912
```

<210> SEQ ID NO 46
<211> LENGTH: 274
<212> TYPE: PRT
<213> ORGANISM: Nannochloropsis gaditana

<400> SEQUENCE: 46

```
Met Leu Cys Cys Ala Cys Lys Ser Val His Ala Thr Ile Ser Val Ala
1               5                  10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
```

Ile Ser

<210> SEQ ID NO 47
<211> LENGTH: 825
<212> TYPE: DNA
<213> ORGANISM: Nannochloropsis gaditana

<400> SEQUENCE: 47

```
atgctatgtt gcgcctgtaa atcagtgcat gcgactatta gtgtcgcctt tattggtact    60
cggaagccac atcgtttgcc tgcattgttt ccattgttcc ttgccccggc ccgagcactc   120
agccatcagg agccgaaccc tgcaacgtgc gggacgcaaa actcatcctt ctcgatcttg   180
ttgaaaacgg tagtagcagg atcattcgtc ggtgcggcat tcatcgctgg catacagca   240
ggggctagct gtgatgaagt aaagtctccg caggaggtga acaatgtagg aggcggcgcc   300
ccagtgactg cccccctacac ggtcactttt gcgtccaatt atcatgatcg agtggacaca   360
aaacttcata gagcttatcc tgagttttta cagtaccatc ttattcatga aacgcttcga   420
ggcaaggaaa agatagaggg ctacgaggtg tacaaagata ggcgtgacga ttctatcgta   480
gcatttgctc gcctcgggaa gcttctcagc gggcatccgg atataatcca tggaggctct   540
atagccgcct tactcgacaa cactatgggc gtggcattct tcgctgccaa taaaggtaat   600
ggcttcactg ccaacctcac aatcaattac aagaggccga tcatttgtgg caccgagatc   660
aaggtcttgg cccgagtgga gcggtttgaa ggacgcaagg ttttcctacg agcagagatt   720
cgagatgcta aggacgaggc agtgttgtac acggaagcca catccctctt cataacttca   780
caaagtcctc tgcttacggg accgaagaag gtggacatca gttag                   825
```

<210> SEQ ID NO 48
<211> LENGTH: 285
<212> TYPE: PRT
<213> ORGANISM: Nannochloropsis granulata

<400> SEQUENCE: 48

```
Met Thr Pro Leu Ala Phe Thr Ala Leu Gly Glu Val Gly Gly Met Leu
  1               5                  10                  15

Ala Ala Ala Cys Val Arg Arg Lys Leu His His Leu Leu Arg Arg Ala
             20                  25                  30

Ala Ser Ser Ser Gln Val Thr Arg Pro Tyr Ser His Ser Thr Ala Asn
         35                  40                  45

Ser Thr His Ser Thr Thr Thr Leu Ser Asn Ser Phe Pro Val Leu Phe
     50                  55                  60

Ala Gln Leu Ala Ala Ala Ala Ala Val Met Ala Ala Thr Ser Leu
 65                  70                  75                  80

Ser Ser Pro Ser Leu Cys Glu Thr Ala His Thr Asn Thr Glu Glu Arg
                 85                  90                  95

Gly Gly Glu Gly Glu Ala Met Arg Glu Lys Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
```

```
              165                 170                 175
Gly Lys Leu Leu Ser Gly His Pro Asp Ile Ile His Gly Gly Ser Ile
            180                 185                 190

Ala Ala Leu Leu Asp Asn Thr Met Gly Val Ala Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285

<210> SEQ ID NO 49
<211> LENGTH: 858
<212> TYPE: DNA
<213> ORGANISM: Nannochloropsis granulata

<400> SEQUENCE: 49
atgacgcctt tggccttcac ggcgctcggc gaggtcggtg gcatgttggc tgctgcctgt      60
gtacgacgga agcttcatca cttgttgcgg cgggcagctt cgtcctccca ggtcactcga     120
ccttacagtc acagcaccgc caacagcaca catagcacca ccacacttag caacagcttt     180
ccagtcctct tgcgcaact cgcagcagcc gctgctgccg tcatggctgc cacttccctg     240
tcgtcgccca gtctatgtga cggccac accaatactg aggagagagg aggcgaaggg     300
gaggcaatga gggagaaggg tggggaaggc gaggccactt cgtctgctac atgcgctcca     360
tctttcttcg agcatcatga tcgcgtcgac acgaagctgc atcgggccta tcccgagttt     420
ctgaagttcc acctcatcca cgagacgctc cgagggaaag agaaaattga tggctacgaa     480
gtatacaaaa acaggcggga cgattcagtt gtggcgtatg ctcgcctggg caaactgctg     540
agcggacacc ctgacataat tcacggaggg tccatcgctg ctttgctgga caacaccatg     600
ggagttgcct ttttcgccgc caagcgcggc aatggtttca cagcaaatct caccatcaac     660
tacaagcgac ccatcacgtg tggcaccgag gtcaaagttc tggctcgagt agagaaggtg     720
gaggggcgca aggtcttttt gcgggctgag atcagggacg ccaaggatga ggctatcctt     780
tacactgaag ccaactccct cttcatcacg tcgcaaagcc ctctattgaa gggcccaaag     840
aaaattgaca ttagctag                                                  858

<210> SEQ ID NO 50
<211> LENGTH: 233
<212> TYPE: PRT
<213> ORGANISM: Symbiodinium microadriaticum

<400> SEQUENCE: 50

Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
```

```
                    50                  55                  60
Leu Leu Asn Leu Gln Arg Glu Met Ala Leu Arg Asp Arg His Asp Lys
 65                  70                  75                  80

Gln Phe Val Trp Gln Thr Cys Ser Gly Gln Gly Lys Ile Glu Asp Cys
                 85                  90                  95

Arg Ile Tyr His Cys Lys Arg Glu Glu Val Asp Arg Glu Val Ser Leu
                100                 105                 110

Asp Ala Pro Glu Met Val Glu Gly Lys Thr Arg Ile Cys Ala Val Met
            115                 120                 125

Arg Val Gly Asp Glu Leu Asn Gly His Pro Gly Leu Leu His Gly Gly
        130                 135                 140

Phe Thr Ala Ala Val Leu Asp Asp Phe Thr Gly Leu Ala Thr Trp Met
145                 150                 155                 160

Glu Lys Gln Ala Gln Ala Leu Asp Lys Asp Ala Ala Ile Phe Thr Ala
                165                 170                 175

His Met Asp Leu Ser Tyr Arg Arg Pro Leu Lys Ala Lys Ser Glu Tyr
            180                 185                 190

Leu Val Glu Val Cys Val Asp Arg Val Glu Arg Gln Lys Lys Val Phe
            195                 200                 205

Leu Asn Ala Ala Ile Tyr Asp Lys Asp Ser His Ala Cys Val Lys Ala
        210                 215                 220

Lys Val Leu Tyr Ile Val Lys Lys Lys
225                 230

<210> SEQ ID NO 51
<211> LENGTH: 702
<212> TYPE: DNA
<213> ORGANISM: Symbiodinium microadriaticum

<400> SEQUENCE: 51
atggctttca ggctatgctc tctttcccgg cggtttgctg cgcacgcgca gcaggtgctg    60
cggaaggagg ctggctttga gttccgcgca agctgcatcg ccattaccgc tggcatctct   120
gctggatggt gcatgcagca ggcagcgcgg gcggagggca tctggactcc gcacctgggc   180
gaggaggcca agttgttgaa cctccagcgc gagatggcgc tgagagacag acacgacaag   240
caatttgtgt ggcagacctg cagtggccag ggcaaaattg aggactgccg catatatcac   300
tgcaagcgag aagaagttga tcgtgaggtt tcgctgacg cgccggaaat ggtgagggc    360 aaaacacgga tttgtgcagt gatgcgcgtt ggcgacgagc tgaacggcca tcctgggctt   420
ttgcatggcg gcttcactgc cgccgtgctg gacgatttca caggcctggc gacctggatg   480
gagaagcaag cgcaggcgct ggacaaggat gcggccattt tcaccgctca catggatctc   540
agctatcggc gaccctgaa ggcgaagtcg gagtacttgg ttgaggtttg cgttgaccgt    600
gttgagcggc aaaagaaggt ctttctgaat gctgccatct atgacaagga cagccatgcc   660
tgcgtgaaag caaggtgtt gtacatcgtc aaaaagaagt ga                       702
```

METHOD OF PRODUCING FATTY ACIDS OR LIPIDS BY USING ACYLTRANSFERASE

TECHNICAL FIELD

The present invention relates to a method of producing lipids. Further, the present invention also relates to an acyltransferase, a gene encoding the same, and a transformant wherein the expression of the gene is enhanced, for use in this method.

BACKGROUND ART

Fatty acids are one of the principal components of lipids. In vivo, fatty acids are bonded to glycerin via an ester bond to form lipids (fats and oils) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary amine salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, lipids derived from plants are also used as raw materials of biodiesel fuels.

Fatty acids and lipids are widely used for various applications shown above, and therefore, it has been attempted to enhance the productivity of fatty acids or lipids in vivo by using plants and the like. Furthermore, the applications and usefulness of fatty acids depend on the number of carbon atoms. Therefore, controlling of the number of carbon atoms of the fatty acids, namely, a chain length thereof has also been attempted.

A fatty acid synthetic pathway of plants is localized in the chloroplast. In the chloroplast, an elongation reaction of the carbon chain is repeated starting from an acetyl-ACP (acyl-carrier-protein), and finally an acyl-ACP (a composite consisting of an acyl group being a fatty acid residue and an ACP) having 16 or 18 carbon atoms is synthesized. The synthesized acyl-ACP is formed into a free fatty acid by an acyl-ACP thioesterase (hereinafter, also simply referred to as "TE"). To the free fatty acid, CoA is bonded by an acyl-CoA synthetase. Then, the fatty acyl-CoA is incorporated into a glycerol skeleton by various acyltransferases, and is accumulated as the triacylglycerol (hereinafter, also simply referred to as "TAG") formed in which three molecules of the fatty acids are ester-bonded with one molecule of glycerol.

In a biosynthesis of the TAG, first, bonding of an acyl group by a glycerol-3-phosphate acyltransferase (hereinafter, also referred to as "GPAT") is caused in the sn-1 position of glycerol-3-phosphate (hereinafter, also referred to as "G3P"), and thus a lysophosphatidic acid (hereinafter, also referred to as "LPA") is produced. Next, bonding of an acyl group by a lysophosphatidic acid acyltransferase (hereinafter, also referred to as "LPAAT") is caused in the sn-2 position of the LPA, and thus a phosphatidic acid (herein after, also referred to as "PA") is produced. Subsequently, dephosphorylation is caused by a phosphatidic acid phosphatase (hereinafter, also referred to as "PAP"), and thus diacylglycerol (hereinafter, also referred to as "DAG") is produced. Finally, an acyl group is bonded therewith in the sn-3 position by a diacylglycerol acyltransferase (hereinafter, also referred to as "DGAT"), and thus the TAG is produced.

In addition, there is also a pathway in which the acyl group in a phospholipid is transformed into the DAG by a phospholipid:diacylglycerol acyltransferase (hereinafter, also referred to as "PDAT") to produce the TAG.

Kinds of fatty acids to be bonded with the glycerol are wide-ranging, and various TAG compounds are formed depending on combinations of the fatty acids to be boded therewith. Then, in plants, the TAG compound is accumulated mainly in seeds or the like as an energy storage substance.

Methods of producing the TAG or the fatty acids have been so far proposed by using various acyltransferases.

For example, a method of producing TAG using *Chlamydomonas reinhardtii* in which DGAT2 is subjected to overexpression is proposed in Patent Literatures 1 and 2. In addition, Patent Literature 3 describes a DGAT derived from *Nannochloropsis oculata*, in which a possibility to be involved in a production of long-chain polyunsaturated fatty acids having 18 or 22 carbon atoms or the like is suggested. Moreover, a method of improving productivity of palmitic acid utilizing a GPAT derived from *Thalassiosira pseudonana* (see Patent Literature 4), a method of improving productivity of TAG utilizing a PDAT derived from *Saccharomyces cerevisiae* (see Patent Literature 5), a method of improving productivity of medium-chain fatty acids utilizing a LPAAT derived from *Cocos nucifera* (see Patent Literature 6), and the like are proposed.

Recently, algae attract attention due to its usefulness in biofuel production. The algae can produce lipids that can be used as the biodiesel fuels through photosynthesis, and do not compete with foods. Therefore, the algae attract attention as next-generation biomass resources. Moreover, it is also reported that the algae have higher lipid productivity and accumulation ability in comparison with plants. Research has started on a lipid synthesis and accumulation mechanism of the algae and lipid production technologies utilizing the mechanism, but unclear parts remain in many respects.

CITATION LIST

Patent Literatures

Patent Literature 1: WO 2011/156520
Patent Literature 2: JP-A-2014-14334 ("JP-A" means unexamined published Japanese patent application)
Patent Literature 3: WO 2011/161093
Patent Literature 4: WO 2009/120366
Patent Literature 5: WO 00/60095
Patent Literature 6: WO 95/27791

SUMMARY OF INVENTION

The present invention relates to a method of producing lipids, containing the steps of:

culturing a transformant wherein the expression of a gene encoding the following protein (A) or (B) is enhanced, and producing fatty acids or lipids containing these fatty acids as components:

(A) A protein consisting of the amino acid sequence set forth in SEQ ID NO: 1; and (B) A protein consisting of an amino acid sequence having 44% or more identity with the amino acid sequence of the protein (A), and having acyltransferase activity.

Further, the present invention relates to the protein (A) or (B).

Further, the present invention relates to a gene encoding the protein (A) or (B).

Furthermore, the present invention relates to a transformant, wherein the expression of a gene encoding the protein (A) or (B) is enhanced.

MODE FOR CARRYING OUT THE INVENTION

The present invention relates to a method of producing lipids, which improves productivity of medium-chain fatty acids or the lipids containing these fatty acids as components, and total amount of the lipids to be produced.

Further, the present invention relates to a transformant in which the productivity of medium-chain fatty acids or the lipids containing these fatty acids as components and total amount of the lipids to be produced are improved.

The present inventors newly identified, as an enzyme involved in a fatty acid synthesis, an acyltransferase (hereinafter, also referred to as "AT") of algae of the genus *Nannochloropsis*, being one kind of algae. Then, the present inventor enhanced an expression of the AT in microorganisms, and as the result, found that the productivity of medium-chain fatty acids or the lipids containing these fatty acids as components to be produced and total amount of the lipids to be produced are significantly improved.

The present invention was completed based on these findings.

According to the method of producing the lipids of the present invention, the productivity of medium-chain fatty acids or the lipids containing these fatty acids as components, and total amount of the lipids to be produced can be improved.

Moreover, the transformant of the present invention is excellent in the productivities of medium-chain fatty acids or the lipids containing these fatty acids as components, and all fatty acids to be produced.

Other and further features and advantages of the invention will appear more fully from the following description.

The term "lipid(s)" in the present specification, covers simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid, alcohols, and hydrocarbons.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The above-described protein (A) or (B) (hereinafter, also referred to as "NoAT", "AT4295", or "NoAT4295") is one of the acyltransferase, and a protein catalyzing the acylation of a glycerol compound such as glycerol-3-phosphate. The protein consisting of the amino acid sequence set forth in SEQ ID NO: 1 is an AT derived from *Nannochloropsis oculata* NIES-2145 being algae belonged to the genus *Nannochloropsis*.

Both proteins (A) and (B) described above have the acyltransferase activity (hereinafter, also referred to as "AT activity"). In the present specification, the term "AT activity" means the activity to catalyze the acylation of a glycerol compound such as glycerol-3-phosphate.

It can be confirmed that the protein has the AT activity by a system using a triacylglycerol synthase gene deletion strain, for example. Alternatively, it can be confirmed by examining whether or not the LPA is synthesized from the G3P, the DAG is synthesized from the LPA or the TAG is synthesized from the DAG in a system formed by introducing, into a host cell, a DNA produced by linking a gene encoding the above-described protein to the downstream of a promoter which functions within the host cell, culturing the obtained cells under conditions in which the gene introduced thereinto is expressed, and then adding, to a homogenate of the cells, acyl-CoA, various phospholipids, various glycolipids or the like as a donor, together with any one of receptors of the G3P, the LPA and the DAG.

By the results of Blast analysis using the amino acid sequence and nucleotide sequence, the proteins (A) and (B) are considered to be one kind of the acyltransferase.

As shown in Examples mentioned later, the productivity of medium-chain fatty acids having 12, 14 or the like carbon atoms and total amount of all fatty acids to be produced are improved in a transformant, wherein the expression of the gene encoding the protein (A) is enhanced.

In addition, in the present specification, the term "medium-chain" means that the number of carbon atoms of the acyl group is 6 or more and less than 14, preferably 8 or more and less than 14, more preferably 10 or more and less than 14, more preferably 12 or more and less than 14, and furthermore preferably 12 or 14.

In the protein (B), the identity with the amino acid sequence of the protein (A) is preferably 45% or more, more preferably 50% or more, further preferably 55% or more, further preferably 60% or more, further preferably 65% or more, further preferably 70% or more, further preferably 75% or more, further preferably 80% or more, further preferably 85% or more, further preferably 90% or more, further preferably 93% or more, further preferably 95% or more, further preferably 96% or more, further preferably 97% or more, further preferably 98% or more, and furthermore preferably 99% or more, in view of AT activity. Further, specific examples of the protein (B) include a protein in which 1 or several, for example 1 or more and 238 or less, preferably 1 or more and 233 or less, more preferably 1 or more and 212 or less, further preferably 1 or more and 191 or less, furthermore preferably 1 or more and 170 or less, furthermore preferably 1 or more and 148 or less, furthermore preferably 1 or more and 127 or less, furthermore preferably 1 or more and 106 or less, furthermore preferably 1 or more and 85 or less, furthermore preferably 1 or more and 63 or less, furthermore preferably 1 or more and 42 or less, furthermore preferably 1 or more and 29 or less, furthermore preferably 1 or more and 21 or less, furthermore preferably 1 or more and 17 or less, furthermore preferably 1 or more and 12 or less, furthermore preferably 1 or more and 8 or less, and furthermore preferably 1 or more and 4 or less amino acids are deleted, substituted, inserted or added to the amino acid sequence of the protein (A).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) and (B) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) and (B) can be obtained by artificial chemical synthesis based on the amino acid sequence set forth in SEQ ID NO: 1. Alternatively, as recombinant proteins, proteins (A) and (B) may also be produced by gene recombination technologies. In the case of producing a recombinant protein, the AT gene described below can be used.

Note that the algae such as *Nannochloropsis oculata* can be obtained from culture collection such as private or public research institutes or the like. For example, *Nannochloropsis oculata* NIES-2145 can be obtained from National Institute for Environmental Studies (NIES).

An example of the gene encoding the protein (A) or (B) (hereinafter, also referred to as "AT gene") includes a gene consisting of the following DNA (a) or (b) (hereinafter, also referred to as "NoAT gene", "AT4295 gene", or "NoAT4295 gene").
(a) a DNA consisting of the nucleotide sequence set forth in SEQ ID NO: 2; and
(b) a DNA consisting of a nucleotide sequence having 51% or more identity with the nucleotide sequence of the DNA (a), and encoding the protein having AT activity.

The nucleotide sequence set forth in SEQ ID NO: 2 is a nucleotide sequence of a gene encoding a protein (AT derived from *Nannochloropsis oculata* NIES-2145) consisting of the amino acid sequence set forth in SEQ ID NO: 1.

In the DNA (b), the identity with the nucleotide sequence of the DNA (a) is preferably 55% or more, more preferably 60% or more, further preferably 65% or more, further preferably 70% or more, further preferably 75% or more, further preferably 80% or more, further preferably 85% or more, further preferably 90% or more, further preferably 93% or more, further preferably 95% or more, further preferably 96% or more, further preferably 97% or more, further preferably 98% or more, and furthermore preferably 99% or more, in view of AT activity. Further, the DNA (b) is also preferably a DNA in which 1 or several, for example 1 or more and 624 or less, preferably 1 or more and 573 or less, more preferably 1 or more and 510 or less, further preferably 1 or more and 446 or less, furthermore preferably 1 or more and 382 or less, furthermore preferably 1 or more and 318 or less, furthermore preferably 1 or more and 255 or less, furthermore preferably 1 or more and 191 or less, furthermore preferably 1 or more and 127 or less, furthermore preferably 1 or more and 89 or less, furthermore preferably 1 or more and 63 or less, furthermore preferably 1 or more and 51 or less, furthermore preferably 1 or more and 38 or less, furthermore preferably 1 or more and 25 or less, and furthermore preferably 1 or more and 12 or less nucleotides are deleted, substituted, inserted or added to the nucleotide sequence set forth in SEQ ID NO: 2, and encoding the protein (A) or (B) having AT activity.

Furthermore, the DNA (b) is also preferably a DNA capable of hybridizing with a DNA consisting of the nucleotide sequence complementary with the DNA (a) under a stringent condition, and encoding the protein having AT activity.

A method of enhancing the expression of the AT gene can be appropriately selected from an ordinarily method. For example, a method of introducing the AT gene into a host, and a method of modifying expression regulation regions of the gene (promoter, terminator, or the like) in a host having the AT gene on a genome, can be selected.

Hereinafter, in the present specification, a cell in which expression of a gene encoding a target protein herein is enhanced is also referred to as the "transformant", and a cell in which the expression of the gene encoding the target protein is not enhanced is also referred to as the "host" or "wild type strain".

In the transformant used in the present invention, the productivity of medium-chain fatty acids or lipids containing these medium-chain fatty acids as components (a production amount of medium-chain fatty acids or lipids containing these medium-chain fatty acids as components, or a ratio of medium-chain fatty acids or lipids containing these medium-chain fatty acids as components in the total fatty acids or total lipids to be produced) is significantly improved, in comparison with a host. Moreover, as a result, in the transformant, the fatty acid composition in the lipid is modified. Therefore, the present invention using the transformant can be preferably applied to production of lipids having specific number of carbon atoms, particularly medium-chain fatty acids or lipids containing these medium-chain fatty acids as components, preferably fatty acids having 6 to 14 carbon atoms or lipids containing these fatty acids as components, more preferably fatty acids having 8 to 14 carbon atoms or lipids containing these fatty acids as components, further preferably fatty acids having 10 to 14 carbon atoms or lipids containing these fatty acids as components, further preferably fatty acids having 12 to 14 carbon atoms or lipids containing these fatty acids as components, furthermore preferably fatty acids having 12 or 14 carbon atoms or lipids containing these fatty acids as components, furthermore preferably saturated fatty acids having 10, 12, or 14 carbon atoms (capric acid, lauric acid, or myristic acid) or lipids containing these fatty acids as components, and furthermore preferably saturated fatty acids having 12 or 14 carbon atoms (lauric acid or myristic acid) or lipids containing these fatty acids as components.

Moreover, in the transformant used in the present invention, the productivity of medium-chain fatty acids or lipids containing these fatty acids as components as well as a total amount of all fatty acids to be produced are significantly improved, in comparison with a host. Therefore, the present invention using the transformant can be preferably applied to production of lipids.

The productivity of fatty acids and lipids of the host and the transformant can be measured by the method used in Examples described below.

The method of introducing the AT gene into a host and enhancing the expression of the gene is described.

The AT gene can be obtained by genetic engineering techniques that are ordinarily carried out. For example, the AT gene can be artificially synthesized based on the amino acid sequence set forth in SEQ ID NO: 1 or the nucleotide sequence set forth in SEQ ID NO: 2. The synthesis of the AT gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the AT gene into the host according to an ordinarily method. Specifically, the transformant can be produced by preparing a recombinant vector or a gene expression cassette which is capable of expressing the AT gene in a host cell, introducing this vector or cassette into the host cell, and thereby transforming the host cell.

The host for the transformant can be appropriately selected from ordinarily used hosts. For example, microorganisms (including algae and microalgae), plants or animals can be used as the host in the present invention. Among these, microorganisms or plants are preferable, microorganisms are more preferable, and microalgae are further preferable as a host, from the viewpoints of production efficiency and the usability of lipids to be obtained.

As the microorganisms, prokaryotes and eukaryotes can be used. Examples of the prokaryotes include microorganisms belonging to the genus *Escherichia*, microorganisms belonging to the genus *Bacillus*, microorganisms belonging to the genus *Synechocystis*, microorganisms belonging to the genus *Synechococcus*, and the like. Examples of the eukaryotes include eukaryotic microorganisms belonging to yeast, filamentous fungi and the like. Among these, from a viewpoint of the productivity of lipids, *Escherichia coli*, *Bacillus subtilis*, *Rhodosporidium toruloides*, or *Mortierella* sp., is preferable, and *Escherichia coli* is more preferable.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferable, and algae belonging to the genus *Nannochloropsis* are more preferable. Specific examples of the algae belonging to the genus *Nannochloropsis* include *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among these, from a viewpoint of the productivity of lipids, *Nannochloropsis oculata* or *Nannochloropsis* gaditana is preferable, and *Nannochloropsis oculata* is more preferable.

As the plants, from a viewpoint of a high lipid content of seeds, *Arabidopsis thaliana*, *Brassica napus*, *Brassica raga*, *Cocos nucifera*, *Elaeis quineensis*, cuphea, *Glycine max*, *Zea mays*, *Oryza sativa*, *Helianthus annuus*, *Cinnamomum camphora*, or *Jatropha curcas* is preferable, and *Arabidopsis thaliana* is more preferable.

A vector for use as the plasmid vector for gene expression or a vector containing the gene expression cassette (plasmid) may be any vector capable of introducing the gene encoding the target protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (McKenzie, T. et al., 1986, Plasmid 15(2), p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(−) or pMW218/219 is preferably used.

When the algae or the microalgae are used as the host, specific examples of the vector include pUC19 (manufactured by Takara Bio), P66 (*Chlamydomonas* Center), P-322 (*Chlamydomonas* Center), pPha-T1 (see Yangmin Gong, et al., Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, 2011, vol. 108(52), by using the DNA fragment consisting of the target gene of the present invention, a promoter and a terminator (gene expression cassette). Specific examples of this DNA fragment include a PCR-amplified DNA fragment and a restriction enzyme-cut DNA fragment.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), *Brassica napus* or *Brassica rapa*-derived *Napin* gene promoter, plant-derived Rubisco promoter, a promoter of a violaxanthin/(chlorophyll a)-binding protein gene derived from the genus *Nannochloropsis* (VCP1 promoter, VCP2 promoter) (Oliver Kilian, et al., Proceedings of the National Academy of Sciences of the United States of America, 2011, vol. 108 (52)), and a promoter of an oleosin-like protein LDSP (lipid droplet surface protein) gene derived from the genus *Nannochloropsis* (Astrid Vieler, et al., PLOS Genetics, 2012, vol. 8(11): e1003064. DOI: 10.1371). In the case of using *Nannochloropsis* as the host in the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

Introduction of the gene encoding a target protein to the vector can be conducted by an ordinary technique such as restriction enzyme treatment and ligation.

Furthermore, the method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. When the algae belonging to the genus *Nannochloropsis* are used as the host, transformation can also be performed by using the electroporation method described in Randor Radakovits, et al., Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In a host having the AT gene on a genome, a method of modifying expression regulation regions of the gene and enhancing the expression of the gene is described.

The "expression regulation region" indicates the promoter or the terminator, in which these sequences are generally involved in regulation of the expression amount (transcription amount, translation amount) of the gene adjacent thereto. In a host having the above-described AT gene on a genome, productivity of medium-chain fatty acids or lipids containing these medium-chain fatty acids as components can be improved by modifying expression regulation regions of the gene and enhancing the expression of the AT gene.

Specific examples of the method of modifying the expression regulation regions include interchange of promoters. In the host having the above-mentioned AT gene on the genome, the expression of the above-described AT gene can be enhanced by interchanging the promoter of the gene (hereinafter, also referred to as "AT promoter") with a promoter having higher transcriptional activity. For example, in *Nannochloropsis oculata* NIES-2145 strain being one of the hosts having the AT genes on the genome, the NoAT gene exists at the downstream of a DNA sequence consisting of the nucleotide sequence set forth in SEQ ID NO: 41, and a promoter region exists in the DNA sequence consisting of the nucleotide sequence set forth in SEQ ID NO: 41. The expression of the above-described AT gene can be enhanced by partially or wholly interchanging the DNA sequences consisting of the nucleotide sequence set forth in SEQ ID NO: 41 with the promoter having higher transcriptional activity.

The promoter used for interchanging the AT promoter is not particularly limited, and can be appropriately selected from the promoters that are higher in the transcriptional activity than the AT promoter and suitable for production of the medium-chain fatty acids or the lipids containing these fatty acids as the components.

When the host is *Nannochloropsis*, a tubulin promoter, a heat shock protein promoter, the above-described promoter of a violaxanthin/(chlorophyll a)-binding protein gene (VCP1 promoter (SEQ ID NO: 35), VCP2 promoter), and a promoter of an oleosin-like protein LDSP gene derived from the genus *Nannochloropsis* (SEQ ID NO: 18), can be preferably used. From a viewpoint of improvement in the productivity of medium-chain fatty acids or lipids containing these medium-chain fatty acids as components, the promoter of a violaxanthin/(chlorophyll a)-binding protein gene and the promoter of LDSP gene are more preferable.

The above-described modification of a promoter can employ according to an ordinarily method such as homologous recombination. Specifically, a linear DNA fragment containing upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. Then the target promoter on the genome is substituted with other promoter fragment, and the promoter can be modified.

The method of modifying a target promoter according to such homologous recombination can be conducted with, for example, reference to literature such as Besher et al., Methods in molecular biology, 1995, vol. 47, p. 291-302. In particular, when the host is the algae belonging to the genus *Nannochloropsis*, specific region in a genome can be modified, with referring to literature such as Oliver Kilian, et al., Proceedings of the National Academy of Sciences of the United States of America, 2011, vol. 108(52), by homologous recombination method.

The transformant of the present invention preferably has enhancing expression of a gene encoding a TE (hereinafter, also referred to as "TE gene"), in addition to the gene encoding the protein (A) or (B)

As described above, TE is an enzyme that hydrolyzes the thioester bond of the acyl-ACP synthesized by a fatty acid synthase such as the β-ketoacyl-ACP synthase (hereinafter, also referred to as "KAS") to produce a free fatty acid. The function of the TE terminates the fatty acid synthesis on the ACP, and then the thus-hydrolyzed fatty acid is supplied to the synthesis of polyunsaturated fatty acid, TAG or the like. Then, the above-described AT is involved in the TAG synthesis or the like.

Therefore, lipid productivity of the transformant to be used for the lipid production, particularly productivity of the fatty acids can be further improved by increasing the content of a substrate for TAG synthesis wherein the AT is involved, due to the enhancing of the expression of the TE gene, in addition to the AT gene. Furthermore, as shown in Examples mentioned later, total amount of the amounts of each of the fatty acids (total amount of the fatty acids) can be also improved by enhancing the expression of the TE gene, in addition to the AT gene.

The TE that can be used in the present invention merely needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE is considered to be an important factor in determining the fatty acid composition of an organism. In particular, when a host originally having no gene encoding a TE is used in the transformation, it is preferable to enhance the expression of the gene encoding a TE. In addition, according to enhancing the expression of the TE gene having substrate specificity to the medium-chain acyl-ACP, the productivity of medium-chain fatty acids is improved. The productivity of medium-chain fatty acids is further improved by introducing such a gene.

The TE that can be used in the present invention can be appropriately selected from ordinary TEs and proteins functionally equivalent to the TEs, according to a kind of host or the like.

Specific examples thereof include TE derived from *Cuphea calophylla* subsp. *mesostemon* (GenBank ABB71581); TE derived from *Cinnamomum camphora* (GenBank AAC49151.1); TE derived from *Myristica fragrans* (GenBank AAB71729); TE derived from *Myristica fragrans* (GenBank AAB71730); TE derived from *Cuphea lanceolata* (GenBank CAA54060); TE derived from *Cuphea hookeriana* (GenBank Q39513); TE derived from *Ulumus americana* (GenBank AAB71731); TE derived from *Sorghum bicolor* (GenBank EER87824); TE derived from *Sorghum bicolor* (GenBank EER88593); TE derived from *Cocos nucifera* (CnFatB1: see Jing et al. BMC Biochemistry 2011, 12:44); TE derived from *Cocos nucifera* (CnFatB2: see Jing et al., BMC Biochemistry, 2011, 12:44); TE derived from *Cuphea viscosissima* (CvFatB1: see Jing et al., BMC Biochemistry, 2011, 12:44); TE derived from *Cuphea viscosissima* (CvFatB2: see Jing et al., BMC Biochemistry, 2011, 12:44); TE derived from *Cuphea viscosissima* (CvFatB3: see Jing et al., BMC Biochemistry, 2011, 12:44); TE derived from *Elaeis quineensis* (GenBank AAD42220); TE derived from *Desuifovibrio vulgaris* (GenBank ACL08376); TE derived from *Bacteroides fragilis* (GenBank CAH09236); TE derived from *Parabacteriodes distasonis* (GenBank ABR43801); TE derived from *Bacteroides thetaiotaomicron* (GenBank AAO77182); TE derived from *Clostridium asparagiforme* (GenBank EEG55387); TE derived from *Bryanthella formatexigens* (GenBank EET61113); TE derived from *Geobacillus* sp. (GenBank EDV77528); TE derived from *Streptococcus dysgalactiae* (GenBank BAH81730); TE derived from *Lactobacillus brevis* (GenBank ABJ63754); TE derived from *Lactobacillus plantarum* (GenBank CAD63310); TE derived from *Anaerococcus tetradius* (GenBank EEI82564); TE derived from *Bdellovibrio bacteriovorus* (GenBank CAE80300); TE derived from *Clostridium thermocellum* (GenBank ABN54268); TE derived from *Nannochloropsis oculata* (hereinafter, also referred to as "NoTE") (SEQ ID NO: 28, nucleotide sequence of a gene encoding thereof; SEQ ID NO: 29); TE derived from *Umbellularia californica* (GenBank AAA34215.1, SEQ ID NO: 42, nucleotide sequence of a gene encoding thereof; SEQ ID NO: 43); TE derived from *Cocos nucifera* (SEQ ID NO: 44, nucleotide sequence of a gene encoding thereof; SEQ ID NO: 45); TE derived from *Nannochloropsis qaditana* (SEQ ID NO: 46, nucleotide sequence of a gene encoding thereof; SEQ ID NO: 47); TE derived from *Nannochloropsis qranulata* (SEQ ID NO: 48, nucleotide sequence of a gene encoding thereof; SEQ ID NO: 49); and TE derived from *Symbiodinium microadriaticum* (SEQ ID NO: 50, nucleotide sequence of a gene encoding thereof; SEQ ID NO: 51).

Moreover, as the proteins functionally equivalent to them, a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the TEs described above, and having TE activity, can be also used. Alternatively, a protein consisting of an amino acid sequence in which 1 or several amino acids, (for example, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, and furthermore preferably 1 or 15 amino acids), are deleted, substituted, inserted or added to the amino acid sequence of any one of the TEs described above, and having TE activity, can be also used.

Among these TEs described above, from a viewpoint of the substrate specificity for medium-chain acyl-ACP, NoTE (SEQ ID NO: 28, nucleotide sequence of a gene encoding thereof; SEQ ID NO: 29), TE derived from *Umbellularia californica* (SEQ ID NO: 42, nucleotide sequence of a gene encoding thereof; SEQ ID NO: 43), TE derived from *Cocos nucifera* (SEQ ID NO: 44, nucleotide sequence of a gene encoding thereof; SEQ ID NO: 45), TE derived from *Nannochloropsis qaditana* (SEQ ID NO: 46, nucleotide sequence of a gene encoding thereof; SEQ ID NO: 47), TE derived from *Nannochloropsis qranulata* (SEQ ID NO: 48, nucleotide sequence of a gene encoding thereof; SEQ ID NO: 49), TE derived from *Symbiodinium microadriaticum* (SEQ ID NO: 50, nucleotide sequence of a gene encoding thereof; SEQ ID NO: 51), a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of any one of the TEs, and having TE activity for medium-chain acyl-ACP (for example, a protein which is encoded by the DNA consisting of the nucleotide sequence set forth in SEQ ID NO: 34), or a protein consisting of an amino acid sequence in which 1 or several amino acids, (for example, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, and furthermore preferably 1 or 15 amino acids), are deleted, substituted, inserted or added to the amino acid sequence of any one of the TEs, and having TE activity for medium-chain acyl-ACP, is preferable.

The sequence information or the like of these TEs and the genes encoding thereof can be obtained from, for example, National Center for Biotechnology Information, NCBI, or the like.

The TE activity of the protein can be confirmed by, for example, introducing a DNA produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by using a gas chromatographic analysis or the like.

Alternatively, the TE activity can be measured by introducing a DNA produced by linking the TE gene to the downstream of a promoter which functions in a host cell such as *Escherichia coli*, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. U.S.A., 1995, vol. 92 (23), p. 10639-10643).

The transformants in which expression of the gene TE is enhanced can be prepared by an ordinary method. For example, the transformants can be prepared by a method similar to the above-mentioned method for enhancing expression of the AT gene, such as a method of introducing a TE gene into a host, and a method of modifying expression regulation regions of a gene in a host having the TE gene on a genome.

Furthermore, in the transformant of the present invention, expression of a gene encoding a KAS or the like, in addition to the above-described gene encoding the protein (A) or (B), is also preferably enhanced.

KAS IV, being one kind of KAS, mainly catalyzes the elongation reaction that the acyl-ACP having 6 carbon atoms is converted to the acyl-ACP having 14 carbon atoms, to synthesize a medium-chain acyl-ACP. Therefore, productivity of medium-chain fatty acids can be further improved by enhancing the expression of the KAS IV gene, in addition to the AT gene.

The KAS that can be used in the present invention can be appropriately selected from ordinary KASs and proteins functionally equivalent to the KASs, according to a kind of host or the like.

Further, the transformants in which expression of the gene KAS is enhanced can be prepared by an ordinary method. For example, the transformants can be prepared by a method similar to the above-mentioned method for enhancing expression of the AT gene, such as a method of introducing a gene encoding a KAS into a host, and a method of modifying expression regulation regions of a gene in a host having the gene encoding a KAS on a genome.

In the transformant of the present invention, productivity of the medium-chain fatty acids or the lipids containing these fatty acids as components is improved in comparison with the host in which the expression of the gene encoding the protein (A) or (B) is not enhanced. Accordingly, if the transformant of the present invention is cultured under suitable conditions and then the medium-chain fatty acids or the lipids containing these fatty acids as components are collected from an obtained cultured product or an obtained growth product, the medium-chain fatty acids or the lipids containing these fatty acids as components can be efficiently produced.

Further, in the transformant, total amount of fatty acids to be produced is also significantly improved in comparison with a host. Therefore, if the transformant of the present invention is cultured under suitable conditions and then the fatty acids or the lipids containing these fatty acids as components are collected from an obtained cultured product or an obtained growth product, the fatty acids or the lipids containing these fatty acids as components can be efficiently produced.

Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of lipids, for example, precursor substances involved in the fatty acid biosynthesis system, such as glycerol, acetic acid or glucose, may be added to the medium.

For example, in the case of using *Escherichia coli* as the host, culturing *Escherichia coli* may be carried out in LB medium or Overnight Express Instant TB Medium (Novagen) at 30° C. to 37° C. for half a day to 1 day.

In the case of using *Arabidopsis thaliana* as the host, for example, growth of *Arabidopsis thaliana* may be carried out at soil under the temperature conditions of 20° C. to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the productivity of lipids and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the amount is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably in the range of 100 to 50,000 lx, more preferably in the range of 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably from 0.03 (which is the same degree as the concentration under atmospheric conditions) to 10%, more preferably from 0.05 to 5%, further preferably from 0.1 to 3%, and furthermore preferably from 0.3 to 1%. A concentration of the carbonate is not particularly limited. When the sodium hydrogen carbonate is used, for example, from viewpoints of the growth promotion and the improvement in the productivity of fatty acids, the concentration is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. From viewpoints of the growth promotion of the algae, the improvement in the productivity of fatty acids, and the reduction of production cost, the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture, or shaking culture is preferred, and aerated and agitated culture is more preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds thereof, in view of usability thereof.

In view of usability for a surfactant or the like, the fatty acid or the ester compound thereof contained in the lipid is preferably a medium-chain fatty acid or an ester compound thereof, more preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 10, 12, or 14 carbon atoms (capric acid, lauric acid, or myristic acid) or a fatty acid ester compound thereof, more preferably a saturated fatty acid having 12 or 14 carbon atoms (lauric acid or myristic acid) or a fatty acid ester compound thereof.

From a viewpoint of the productivity, the fatty acid ester compound is preferably a simple lipid or a complex lipid, more preferably a simple lipid, and furthermore preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of improving productivity of lipids, methods of modifying composition of fatty acids to be produced, proteins, genes, recombinant vectors, organisms, transformants, and methods of preparing transformants, described below.

<1> A method of producing lipids, containing the steps of:
culturing a transformant in which the expression of a gene encoding the following protein (A) or (B) is enhanced, and
producing fatty acids or lipids containing these fatty acids as components:

(A) a protein consisting of the amino acid sequence set forth in SEQ ID NO: 1; and
(B) a protein consisting of an amino acid sequence having 44% or more, preferably 45% or more, further preferably 50% or more, furthermore preferably 55% or more, furthermore preferably 60% or more, furthermore preferably 65% or more, furthermore preferably 70% or more, furthermore preferably 75% or more, furthermore preferably 80% or more, furthermore preferably 85% or more, furthermore preferably 90% or more, furthermore preferably 93% or more, furthermore preferably 95% or more, furthermore preferably 96% or more, furthermore preferably 97% or more, furthermore preferably 98% or more, and furthermore preferably 99% or more identity with the amino acid sequence of the protein (A), and having AT activity.

<2> A method of improving lipid productivity, containing the steps of:
  enhancing the expression of a gene encoding the protein (A) or (B) in a transformant, and
  improving the productivity of medium-chain fatty acids or lipids containing these fatty acids as components, produced in a cell of the transformant.

<3> A method of improving lipid productivity, containing the steps of:
  enhancing the expression of a gene encoding the protein (A) or (B) in a transformant, and
  improving the total amount of all fatty acids produced in a cell of the transformant.

<4> A method of modifying the composition of lipids, containing the steps of:
  enhancing the expression of a gene encoding the protein (A) or (B) in a transformant, and
  improving the productivity of medium-chain fatty acids or lipids containing these fatty acids as components produced in a cell of the transformant, to modify the composition of fatty acids or lipids in all fatty acids or all lipids to be produced.

<5> The method described in any one of the above items <1> to <4>, wherein the gene encoding the protein (A) or (B) is introduced into a host, to enhance the expression of the gene.

<6> A method of producing lipids, containing the steps of:
  culturing a transformant into which a gene encoding the protein (A) or (B) is introduced, and
  producing fatty acids or lipids containing these fatty acids as components.

<7> A method of improving lipid productivity, containing the steps of:
  introducing a gene encoding the protein (A) or (B) into a host, and thereby producing a transformant, and
  improving productivity of medium-chain fatty acids or lipids containing these fatty acids as components produced in a cell of the transformant.

<8> A method of improving lipid productivity, containing the steps of:
  introducing a gene encoding the protein (A) or (B) into a host, and thereby producing a transformant, and
improving the total amount of all fatty acids produced in a cell of the transformant.

<9> A method of modifying the composition of lipids, containing the steps of:
  introducing a gene encoding the protein (A) or (B) into a host, and thereby producing a transformant, and
  enhancing productivity of medium-chain fatty acids or lipids containing these fatty acids as components produced in a cell of the transformant, to modify the composition of fatty acids or lipids in all fatty acids or all lipids to be produced.

<10> The method described in any one of the above items <1> to <9>, wherein the protein (B) consists of an amino acid sequence in which 1 or several, preferably 1 or more and 238 or less, preferably 1 or more and 233 or less, more preferably 1 or more and 212 or less, further preferably 1 or more and 191 or less, furthermore preferably 1 or more and 170 or less, furthermore preferably 1 or more and 148 or less, furthermore preferably 1 or more and 127 or less, furthermore preferably 1 or more and 106 or less, furthermore preferably 1 or more and 85 or less, furthermore preferably 1 or more and 63 or less, furthermore preferably 1 or more and 42 or less, furthermore preferably 1 or more and 29 or less, furthermore preferably 1 or more and 21 or less, furthermore preferably 1 or more and 17 or less, furthermore preferably 1 or more and 12 or less, furthermore preferably 1 or more and 8 or less, and furthermore preferably 1 or more and 4 or less amino acids are deleted, substituted, inserted or added to the amino acid sequence of the protein (A).

<11> The method described in any one of the above items <1> to <10>, wherein a gene encoding the protein (A) or (B) is a gene consisting of the following DNA (a) or (b):
(a) a DNA consisting of the nucleotide sequence set forth in SEQ ID NO: 2; and
(b) a DNA consisting of a nucleotide sequence having 51% or more, preferably 55% or more, more preferably 60% or more, further preferably 65% or more, furthermore preferably 70% or more, furthermore preferably 75% or more, furthermore preferably 80% or more, furthermore preferably 85% or more, furthermore preferably 90% or more, furthermore preferably 93% or more, furthermore preferably 95% or more, furthermore preferably 96% or more, furthermore preferably 97% or more, furthermore preferably 98% or more, and furthermore preferably 99% or more, identity with the nucleotide sequence of the DNA (a), and encoding the protein having AT activity.

<12> The method described in the above item <11>, wherein the DNA (b) is a DNA consisting of a nucleotide sequence in which 1 or several, preferably 1 or more and 624 or less, more preferably 1 or more and 573 or less, further preferably 1 or more and 510 or less, furthermore preferably 1 or more and 446 or less, furthermore preferably 1 or more and 382 or less, furthermore preferably 1 or more and 318 or less, furthermore preferably 1 or more and 255 or less, furthermore preferably 1 or more and 191 or less, furthermore preferably 1 or more and 127 or less, furthermore preferably 1 or more and 89 or less, furthermore preferably 1 or more and 63 or less, furthermore preferably 1 or more and 51 or less, furthermore preferably 1 or more and 38 or less, furthermore preferably 1 or more and 25 or less, and furthermore preferably 1 or more and 12 or less nucleotides are deleted, substituted, inserted or added to the nucleotide sequence of the DNA (a), and encoding the protein having AT activity, or a DNA capable of hybridizing with a DNA consisting of the nucleotide sequence complementary with the DNA (a) under a stringent condition, and encoding the protein having AT activity.

<13> The method described in any one of the above items <1> to <12>, wherein expression of a gene encoding a TE is enhanced in the transformant.

<14> The method described in the above item <13>, wherein the TE is a TE having substrate specificity to a medium-chain acyl-ACP.

<15> The method described in the above item <13> or <14>, wherein the TE is a protein consisting of the amino acid sequence set forth in SEQ ID NO: 28, SEQ ID NO: 42, SEQ ID NO: 44, SEQ ID NO: 46, SEQ ID NO: 48, or SEQ ID NO: 50; a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of the protein, and having TE activity for medium-chain acyl-ACP; or a protein consisting of an amino acid sequence in which 1 or several amino acids, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, or furthermore preferably 1 or 15 amino acids are deleted, substituted, inserted or added to the amino acid sequence of the protein, and having TE activity for medium-chain acyl-ACP.

<16> The method described in any one of the above items <1> to <15>, wherein the transformant is a microorganism or a plant.

<17> The method described in the above item <16>, wherein the microorganism is a microalga.

<18> The method described in the above item <17>, wherein the microalga is an alga belonging to the genus *Nannochloropsis*, preferably *Nannochloropsis oculata*.

<19> The method described in the above item <16>, wherein the microorganism is *Escherichia coli*.

<20> The method described in the above item <16>, wherein the plant is *Arabidopsis thaliana*.

<21> The method described in any one of the above items <1> to <20>, wherein the lipids contain a medium-chain fatty acid or an ester compound thereof, preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 10, 12, or 14 carbon atoms (capric acid, lauric acid, or myristic acid) or a fatty acid ester compound thereof, more preferably a saturated fatty acid having 12 or 14 carbon atoms (lauric acid or myristic acid) or a fatty acid ester compound thereof.

<22> The protein (A) or (B) specified in any one of the above items <1> to <21>.

<23> A gene encoding the protein described in the above item <22>.

<24> A gene consisting of the DNA (a) or (b) specified in any one of the above items <1> to <21>.

<25> A recombinant vector, containing the gene described in the above item <23> or <24>.

<26> A transformant, wherein the expression of the gene described in the above item <23> or <24> is enhanced, and at least either of the productivity of medium-chain fatty acids or lipids containing these fatty acids as components, and the total amount of all fatty acids produced in a cell of the transformant is improved.

<27> A transformant, which is obtained by introducing the gene described in the above item <23> or <24> or the recombinant vector described in the above item <25> into a host.

<28> A method of producing a transformant, containing introducing the gene described in the above item <23> or <24> or the recombinant vector described in the above item <25> into a host.

<29> The transformant or the method of producing the same described in any one of the above items <26> to <28>, wherein expression of a gene encoding a TE is enhanced.

<30> The transformant or the method of producing the same described in the above item <29>, wherein the TE is a TE having substrate specificity to a medium-chain acyl-ACP.

<31> The transformant or the method of producing the same described in the above item <29> or <30>, wherein the TE is a protein consisting of the amino acid sequence set forth in SEQ ID NO: 28, SEQ ID NO: 42, SEQ ID NO: 44, SEQ ID NO: 46, SEQ ID NO: 48, or SEQ ID NO: 50; a protein consisting of an amino acid sequence having 50% or more, preferably 60% or more, more preferably 65% or more, more preferably 70% or more, more preferably 75% or more, more preferably 80% or more, more preferably 85% or more, more preferably 90% or more, and further preferably 95% or more identity with the amino acid sequence of the protein, and having TE activity for medium-chain acyl-ACP; or a protein consisting of an amino acid sequence in which 1 or several amino acids, preferably 1 or more and 149 or less amino acids, more preferably 1 or more and 119 or less amino acids, further preferably 1 or more and 104 or less amino acids, furthermore preferably 1 or more and 90 or less amino acids, furthermore preferably 1 or more and 75 or less amino acids, furthermore preferably 1 or more and 60 or less amino acids, furthermore preferably 1 or more and 45 or less amino acids, furthermore preferably 1 or more and 30 or less amino acids, or furthermore preferably 1 or 15 amino acids are deleted, substituted, inserted or added to the amino acid sequence of the protein, and having TE activity for medium-chain acyl-ACP.

<32> The transformant or the method of producing the same described in any one of the above items <26> to <31>, wherein the transformant or the host is a microorganism or a plant.

<33> The transformant or the method of producing the same described in the above item <32>, wherein the microorganism is a microalga.

<34> The transformant or the method of producing the same described in the above item <33>, wherein the microalga is an alga belonging to the genus *Nannochloropsis*, more preferably *Nannochloropsis oculata*.

<35> The transformant or the method of producing the same described in the above item <32>, wherein the microorganism is *Escherichia coli*.

<36> The transformant or the method of producing the same described in the above item <32>, wherein the plant is *Arabidopsis thaliana*.

<37> Use of the protein, the gene, the recombinant vector, the transformant or a transformant obtained by the method of producing a transformant described in any one of the above items <22> to <36>, for producing lipids.

<38> The use described in the above item <37>, wherein the lipids contain a medium-chain fatty acid or an ester compound thereof, preferably a fatty acid having 6 or more and 14 or less carbon atoms or an ester compound thereof, more preferably a fatty acid having 8 or more and 14 or less carbon atoms or an ester compound thereof, more preferably a fatty acid having 10 or more and 14 or less carbon atoms or an ester compound thereof, more preferably a fatty acid having 12 or more and 14 or less carbon atoms or an ester compound thereof, more preferably a fatty acid having 12 or 14 carbon atoms or an ester compound thereof, more preferably a saturated fatty acid having 10, 12, or 14 carbon atoms (caprin acid, lauric acid, or myristic acid) or a fatty acid ester compound thereof, more preferably a saturated fatty acid having 12 or 14 carbon atoms (lauric acid or myristic acid) or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No. | Nucleotide sequence (5'→3') | SEQ ID NO: |
|---|---|---|
| 5 | tctttttttgtgaagcatgattgaacaagatggatt | SEQ ID NO: 5 |
| 6 | tttcccccatcccgatcagaagaactcgtcaagaa | SEQ ID NO: 6 |
| 7 | cgagctcggtacccgactgcgcatggattgaccga | SEQ ID NO: 7 |
| 8 | atatcaagaagctgtctttt | SEQ ID NO: 8 |
| 9 | tcgggatggggggaaaaaaacctctg | SEQ ID NO: 9 |
| 10 | actctagaggatccccttcgtaaataaatcagctc | SEQ ID NO: 10 |
| 12 | gggatcctctagagtcgacctgcaggcatgcaagc | SEQ ID NO: 12 |
| 13 | cgggtaccgagctcgaattc | SEQ ID NO: 13 |
| 14 | cagcccgcatcaacaatgagcaagtcctccttcat | SEQ ID NO: 14 |
| 15 | ctcttccacagaagcttaatggtactgcacagaca | SEQ ID NO: 15 |
| 16 | cgagctcggtacccgttcttccgcttgttgctgcc | SEQ ID NO: 16 |
| 17 | tgttgatgcgggctgagattggtgg | SEQ ID NO: 17 |
| 20 | gcttctgtggaagagccagtg | SEQ ID NO: 20 |
| 21 | caatccatgcgcagtctgatcttgtccatctcgtg | SEQ ID NO: 21 |
| 22 | actgcgcatggattgaccga | SEQ ID NO: 22 |
| 24 | tccgagcagattatggccaagctgaccagcgc | SEQ ID NO: 24 |
| 25 | tttcccccatcccgattagtcctgctcctcggccac | SEQ ID NO: 25 |
| 26 | gcggccgctctagagtgcgagacggcccacgccgggac | SEQ ID NO: 26 |
| 27 | acaaaatattaacgcctagctaatatcaattttctttgg | SEQ ID NO: 27 |
| 30 | ctctagagcggccgccaccg | SEQ ID NO: 30 |
| 31 | gcgttaatattttgttaaaattcg | SEQ ID NO: 31 |
| 32 | ctggacaataccatgggatgggcttttttcgccgccaag | SEQ ID NO: 32 |
| 33 | catggtattgtccagcaaag | SEQ ID NO: 33 |
| 37 | cgagctcggtacccgggcggtcttttgtcctttcctc | SEQ ID NO: 37 |
| 38 | aatctgctcggaggggaggatc | SEQ ID NO: 38 |
| 39 | ccctccgagcagattatgaagaccgccgctctcctc | SEQ ID NO: 39 |
| 40 | gcgcgcaacaccgcgggtgcgggagaac | SEQ ID NO: 40 |

Example 1

(1) Construction of Plasmid for Neomycin Resistance Gene Expression

A neomycin resistance gene (SEQ ID NO: 3), and a tubulin promoter sequence (SEQ ID NO: 4) derived from *Nannochloropsis qaditana* strain CCMP 526 described in a literature (Randor Radakovits, et al., Nature Communications, DOI:10.1038/ncomms1688, 2012) were artificially synthesized. Using the thus-synthesized DNA fragments as a template, and a pair of the primer Nos. 5 and 6, and a pair of the primer Nos. 7 and 8 shown in Table 1, PCRs were carried out, to amplify the neomycin resistance gene and the tubulin promoter sequence, respectively.

Further, using a genome of *Nannochloropsis oculata* strain NIES-2145 as a template, and a pair of the primer Nos. 9 and 10 shown in Table 1, PCR was carried out to amplify the heat shock protein terminator sequence (SEQ ID NO: 11).

Furthermore, using a plasmid vector pUC19 (manufactured by Takara Bio) as a template, and a pair of the primer Nos. 12 and 13 shown in Table 1, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for neomycin resistance gene expression.

Herein, the expression plasmid consisted of the pUC19 vector sequence and an insert sequence in which the tubulin promoter sequence, the neomycin resistance gene and the heat shock protein terminator sequence were linked in this order.

(2) Construction of Plasmid for NoAT4295 Gene Expression

Using a pair of the primer Nos. 14 and 15 shown in Table 1 and a genome of *Nannochloropsis oculata* strain NIES-2145 as a template, PCR was carried out to prepare a NoAT4295 gene fragment.

Further, using a genome of *Nannochloropsis oculata* strain NIES-2145 as a template, and a pair of the primer Nos. 16 and 17 shown in Table 1, PCR was carried out to amplify the LDSP promoter sequence (SEQ ID NO: 18).

Furthermore, a VCP1 terminator sequence (SEQ ID NO: 19) was artificially synthesized based on the complete cds sequence (Accession number: JF957601.1) of the VCP1 (violaxanthin/(chlorophyll a)-binding protein) gene of *Nannochloropsis* sp. strain W2J3B registered in GenBank. Using the thus-synthesized DNA fragments as a template, and a pair of the primer Nos. 20 and 21 shown in Table 1, PCR was carried out to prepare the VCP1 terminator sequence.

Furthermore, using the above-described plasmid for neomycin resistance gene expression as a template, and a pair of the primer Nos. 22 and 13 shown in Table 1, PCR was carried out to amplify a fragment containing the cassette for neomycin resistance gene expression (the tubulin promoter sequence, the neomycin resistance gene, and the heat shock protein terminator sequence) and the pUC19 vector sequence.

These four fragments were fused by a method in a manner similar to described above, to construct plasmids for NoAT4295 gene expression.

Herein, the expression plasmid consisted of the pUC19 vector sequence and an insert sequence in which the LDSP promoter sequence, the NoAT4295 gene, the VCP1 terminator sequence, the tubulin promoter sequence, the neomycin resistance gene and the heat shock protein terminator sequence were linked in this order.

(3) Introduction of a NoAT4295 Gene into *Nannochloropsis oculata*

Using the above-described plasmid for the NoAT4295 gene expression as a template, and a pair of the primer Nos. 16 and 10 shown in Table 1, PCR was carried out to amplify the fragment for NoAT4295 gene expression (a DNA fragment containing the LDSP promoter sequence, the NoAT4295 gene, the VCP1 terminator sequence, the tubulin promoter sequence, the neomycin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oculata* strain NIES-2145 (obtained from National Institute for Environmental Studies (NIES)) were washed with 384 mM sorbitol solution to completely remove a salt, and the resultant was used as a host cell for transformation. The fragment for NoAT4295 gene expression as amplified above was mixed by about 500 ng with the host cell, and electroporation was carried out under the conditions of 50 μF, 500Ω and 2,200 v/2 mm.

After one day recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant was inoculated in f/2 agar medium containing neomycin, and cultured for two to three weeks under 12 h/12 h light-dark conditions at 25° C. under an atmosphere of 0.3% $CO_2$. Obtained colonies were selected as the modified NoAT4295 transgenic strain (NoAT4295).

(4) Production of Fatty Acids Using the Transformant

The selected strain was inoculated to 50 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 10 mL of the preculture fluid was inoculated to 40 mL of the N15P5 medium, and subjected to shaking culture under the 12 h/12 h light-dark conditions at 25° C. under the atmosphere of 0.3% $CO_2$. After three weeks cultivation, lipid components contained in the culture fluid were analyzed by the method described below.

(5) Extraction of Lipids and Analysis of Fatty Acids Contained Therein

To 1 mL of the culture fluid, 50 μL of 1 mg/mL 7-pentadecanone as an internal standard was added, and then 0.5 mL of chloroform, 1 mL of methanol and 10 μL of 2N hydrochloric acid were further added. The mixture was vigorously stirred and then was left for 30 minutes. Further, 0.5 mL of chloroform and 0.5 mL of 1.5% KCl were added thereto. The mixture was stirred and centrifuged for 15 minutes at 3,000 rpm, and then the chloroform layer (lower layer) was collected with Pasteur pipette.

A nitrogen gas was blown onto the resultant chloroform layer to be dried into solid. Then, 0.7 mL of 0.5 N potassium hydroxide/methanol solution was added to the sample, and the mixture was kept warm at 80° C. for 30 minutes. Next, 1 mL of 14% boron trifluoride-methanol solution (manufactured by Sigma-Aldrich) was added to the sample, and the mixture was kept warm at 80° C. for 10 minutes. Thereafter, 1 mL of hexane and 1 mL of saturated saline were added thereto, and the mixture was vigorously stirred and then was left for 30 minutes at room temperature. Then, the hexane layer was collected to obtain fatty acid methyl esters.

Under the measuring conditions as follows, the obtained fatty acid methyl esters were provided for gas chromatographic analysis.

<Gas Chromatography Conditions>
Capillary column: DB-1 MS (30 m×200 μm×0.25 μm, manufactured by J & W Scientific)
Mobile phase: high purity helium
Flow rate in column: 1.0 mL/minute
Elevated temperature program: 100° C. (1 minute)→10° C./minute→300° C. (5 minutes)
Equilibrating time: 1 minute
Injection port: split injection (split ratio: 100:1), pressure: 14.49 psi, 104 mL/minute
Amount of injection: 1 μL
Cleaning vial: methanol/chloroform
Detector temperature: 300° C.

Moreover, the fatty acid methyl esters were identified by providing the identical sample under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of all fatty acids (FA) was calculated by summing the amounts of each of the fatty acids thus obtained, and ratio of each of the fatty acids in the total amount of the fatty acids was calculated.

Table 2 shows the results. Herein, in Table below, "Fatty Acid Composition (% TFA)" presents a ratio of a weight of each fatty acid relative to a weight of the total fatty acid (weight percent). Herein, "n" designates an integer of 0 to 5. For example, when "C18:n" is described, the description means a total of each fatty acid having compositions of C18:0, C18:1, C18:2, C18:3, C18:4 and C18:5.

TABLE 2

| | Fatty acid composition (% TFA) | | | | | | |
|---|---|---|---|---|---|---|---|
| | C12:0 | C14:0 | C16:1 | C16:0 | C18:n | C20:n | FA (mg/L) |
| WT | 0.3 ± 0.0 | 5.6 ± 0.1 | 27.9 ± 0.4 | 36.1 ± 0.4 | 11.9 ± 0.2 | 18.2 ± 0.8 | 1878.5 ± 109.0 |
| NoAT4295 | 0.6 ± 0.1 | 11.4 ± 1.0 | 22.9 ± 1.9 | 28.9 ± 2.6 | 17.0 ± 1.8 | 19.1 ± 2.5 | 2284.2 ± 227.1 |

As shown in Table 2, it was confirmed that the ratios of medium-chain fatty acids (lauric acid (C12:0) and myristic acid (C14:0)) and the total amount of all fatty acids were significantly increased, by introducing the NoAT4295 gene.

Example 2

(1) Construction of Plasmid for Zeocin Resistance Gene Expression

A zeocin resistance gene (SEQ ID NO: 23) was artificially synthesized. Using a pair of the primer Nos. 24 and 25 shown in Table 1 and thus-synthesized DNA fragment as a template, PCR was carried out to amplify the zeocin resistance gene fragment.

Using the plasmid for neomycin resistance gene expression prepared in Example 1 as a template, and a pair of the primer Nos. 9 and 8 shown in Table 1, PCR was carried out to amplify the DNA fragment containing the heat shock protein terminator sequence, pUC19 vector sequence, and the tubulin promoter sequence.

The obtained two DNA fragments were fused by a method in a manner similar to that described above, to construct a plasmid for zeocin resistance gene expression.

Herein, the expression plasmid consisted of the pUC19 vector sequence and an insert sequence in which the tubulin promoter sequence, the zeocin resistance gene, and the heat shock protein terminator sequence were linked in this order.

(2) Obtaining of a NoTE Gene and Construction of Plasmid for NoTE Gene Expression

*Nannochloropsis oculata* strain NIES-2145 was obtained from National Institute for Environmental Studies (NIES) so as to be used. *Nannochloropsis oculata* strain NIES-2145 was fully cultured in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), and then, the resultant was inoculated in 50 mL of f/2 medium so as to be 10% of the resultant in the f/2 medium, and cultured for six days at 25° C. under an atmosphere of 0.3% $CO_2$. After culturing, collected samples were crushed by using Multi-beads shocker, and then RNA purification was conducted using RNeasy Plant Mini Kit (manufactured by Qiagen). The cDNA library was prepared by thus-obtained total RNA, using SuperScript III First-Strand Synthesis System for RT-PCR (manufactured by invitrogen).

Using the obtained cDNA as a template, and a pair of the primer Nos. 26 and 27 shown in Table 1, PCR was carried out to prepare the gene fragments consisting of the nucleotide sequence of the 262nd to 864th positions set forth in SEQ ID NO: 29.

Further, using the plasmid vector of pBluescriptII SK(−) (manufactured by Stratagene) as a template, and a pair of the primer Nos. 30 and 31 shown in Table 1, PCR was carried out to amplify the pBluescriptII SK(−), then the template was digested by restriction enzyme DpnI (manufactured by TOYOBO).

These two fragments were purified using a High Pure PCR Product Purification Kit (manufactured by Roche Applied Science). Then, the obtained two fragments were fused using an In-Fusion HD Cloning Kit (manufactured by Clontech) to construct a plasmid NoTE_262 for NoTE gene expression. This plasmid NoTE_262 was constructed for expression of a protein in the form of removing amino acid residues of the 1st to 87th positions on an N-terminal side of the amino acid sequence set forth in SEQ ID NO: 28, and fusing, to the upstream of the removed terminus, amino acid residues of the 1st to 29th positions on an N-terminal side of a LacZ protein derived from the plasmid vector pBluescriptII SK(−).

In the following plasmid notation, "NoTE_262" means that a plasmid had the nucleotide sequence of the 262nd to 864th positions set forth in SEQ ID NO: 29 as a nucleotide sequence encoding a polypeptide consisting of the amino acid sequence of the 88th to 287th positions set forth in SEQ ID NO: 28.

(3) Construction of a Plasmid for the Modified NoTE Gene Expression

PCR was carried out by using the plasmid NoTE_262 as a template, and a pair of the primer Nos. 32 and 33 shown in Table 1, to obtain gene fragments (SEQ ID NO: 34) in which a part of nucleotides of the 262nd to 864th positions of the nucleotide sequence set forth in SEQ ID NO: 29 was subjected to mutation. The plasmids for modified NoTE expression NoTE_262 (V204W), was constructed by using the gene fragment according to a technique in a manner similar to the above-described manner. Herein, the nucleotide sequence set forth in SEQ ID NO: 34 is the nucleotide sequence wherein a codon encoding valine of the 204th position of the amino acid sequence set forth in SEQ ID NO: 28 was substituted with a codon encoding tryptophan (TGG).

Using the plasmid NoTE_262 (V204W) as a template, and a pair of the primer Nos. 31 and 32 shown in Table 1, PCR was carried out to prepare a modified NoTE gene fragment consisting of the nucleotide sequence set forth in SEQ ID NO: 34.

Further, a VCP1 promoter sequence (SEQ ID NO: 35), a VCP1 chloroplast transit signal sequence (SEQ ID NO: 36) and a VCP1 terminator sequence (SEQ ID NO: 19) were artificially synthesized based on the complete cds sequence (Accession number: JF957601.1) of the VCP1 gene of Nannochloropsis sp. strain W2J3B registered in GenBank. Using the thus-synthesized DNA fragments as a template, and a pair of the primer Nos. 37 and 38, a pair of the primer Nos. 39 and 40, and a pair of the primer Nos. 20 and 21 shown in Table 1, PCRs were carried out, to prepare the VCP1 promoter sequence, VCP1 chloroplast transit signal sequence, and VCP1 terminator sequence, respectively.

Furthermore, using a plasmid vector pUC19 (manufactured by Takara Bio) as a template, and a pair of the primer Nos. 12 and 13 shown in Table 1, PCR was carried out to amplify the plasmid vector pUC19.

The modified NoTE gene fragment, the VCP1 promoter sequence, the VCP1 chloroplast transit signal sequence, and the VCP1 terminator sequence were fused with plasmid vector pUC19 by a method in a manner similar to that described above, to construct a plasmid NoTE_262(V204W)_Nanno for modified NoTE gene expression. Herein, the expression plasmid consisted of the pUC19 vector sequence and a sequence for NoTE gene expression in which the VCP1 promoter sequence, the VCP1 chloroplast transit signal sequence, the modified NoTE gene fragment, and the VCP1 terminator sequence were linked in this order.

Using the plasmid NoTE_262 (V204W)_Nanno as a template, and a pair of the primer Nos. 37 and 21 shown in Table 1, PCR was carried out to prepare a gene fragment consisted of the VCP1 promoter sequence, the VCP1 chloroplast transit signal sequence, the NoTE gene, and the VCP1 terminator sequence.

Further, the plasmid for zeocin resistance gene expression as a template, and a pair of the primer Nos. 22 and 13 shown in Table 1, PCR was carried out to amplify a gene fragment consisted of the tubulin promoter sequence, the zeocin resistance gene, the heat shock protein terminator sequence, and the pUC19 vector sequence.

The obtained gene fragments were fused by a method in a manner similar to that described above, to construct a plasmid for modified NoTE gene expression.

Herein, the expression plasmid consisted of the pUC19 vector sequence and an insert sequence in which the VCP1 promoter sequence, the VCP1 chloroplast transit signal sequence, the modified NoTE gene fragment, the VCP1 terminator sequence, the tubulin promoter sequence, the zeocin resistance gene, and the heat shock protein terminator sequence were linked in this order.

(4) Introduction of a Modified NoTE Gene and a NoAT4295 Gene into Nannochloropsis oculata Using the above-described plasmid for the modified NoTE gene expression as a template, and a pair of the primer Nos. 37 and 10 shown in Table 1, PCR was carried out to amplify the fragment for modified NoTE gene expression (a DNA fragment consisted of the VCP1 promoter sequence, the VCP1 chloroplast transit signal sequence, the modified NoTE gene, the VCP1 terminator sequence, the tubulin promoter sequence, the zeocin resistance gene, and the heat shock protein terminator sequence).

The amplified gene fragment was purified using High Pure PCR Product Purification Kit (manufactured by Roche Applied Science). Herein, sterilized water was used for elution upon purification without using an elution buffer included in the kit.

About $1 \times 10^9$ cells of Nannochloropsis oculata strain NIES-2145 (obtained from National Institute for Environmental Studies (NIES)) were washed with 384 mM sorbitol solution to completely remove a salt, and the resultant was used as a host cell for transformation. The fragment for the modified NoTE gene expression as amplified above was mixed by about 500 ng with the host cell, and electroporation was carried out under the conditions of 50 μF, 500Ω and 2,200 v/2 mm.

After one day recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant was inoculated in f/2 agar medium containing 2 μg/mL of zeocin, and cultured for two to three weeks under 12 h/12 h light-dark conditions at 25° C. under an atmosphere of 0.3% $CO_2$. Obtained colonies were selected as the modified NoTE transgenic strain (NoTE).

Using the above-described plasmid for the NoAT4295 gene expression as a template, and a pair of the primer Nos. 16 and 10 shown in Table 1, PCR was carried out to amplify the fragment for NoAT4295 gene expression (a DNA fragment consisted of the LDSP promoter sequence, the NoAT4295 gene, the VCP1 terminator sequence, the tubulin promoter sequence, the neomycin resistance gene, and the heat shock protein terminator sequence).

The gene fragment was introduced into the modified NoTE transgenic strain (NoTE) as a host, by a method in a manner similar to that described above, then obtained colonies in the medium having neomycin were selected as NoTE transgenic strain, and NoTE and NoAT4295 transgenic strain (NoTE+NoAT4295).

(5) Production of Fatty Acids Using the Transformant, Extraction of Lipids and Analysis of Fatty Acids Contained Therein Thus-selected transformants were cultured according to the same method as in Example 1, and extraction of lipids and analysis of fatty acids contained therein were carried out. Table 3 shows the results.

TABLE 3

| | Fatty acid composition (% TFA) | | | | | | | FA (n = 3) |
|---|---|---|---|---|---|---|---|---|
| | C10:0 | C12:0 | C14:0 | C16:1 | C16:0 | C18:n | C20:n | (mg/L) |
| NoTE | 2.5 ± 0.0 | 9.2 ± 0.2 | 13.7 ± 2.5 | 28.5 ± 1.0 | 15.4 ± 0.8 | 15.6 ± 0.5 | 15.0 ± 1.2 | 3037.9 ± 156.7 |
| NoTE + AT4295 | 3.9 ± 0.0 | 11.6 ± 0.1 | 17.8 ± 0.1 | 22.1 ± 0.1 | 15.1 ± 0.4 | 14.3 ± 0.1 | 15.1 ± 0.5 | 4536.1 ± 320.9 |

As shown in Table 3, it was confirmed that the ratios of medium-chain fatty acids (capric acid (C10:0), lauric acid (C12:0), and myristic acid (C14:0)) and the total amount of all fatty acids was significantly increased, by introducing the NoAT4295 gene into the strain into which the modified NoTE gene had been introduced.

(6) Fractionation of TAG and Analysis of Fatty Acids Contained in TAG

The collected chloroform layer was provided for thin-layer chromatography (TLC), and then the TAG was separately collected. As an internal standard, 50 μL of 1 mg/mL triheptadecan was used. The Glass TLC plate 60 (manufactured by Merck) was used for TLC plate, and the resultant was developed using hexane:diethyl ether:formic acid=42:28:0.3 (volume ratio) as a developing solvent. After development, the plate was naturally dried, 0.0001% primulin was sprayed thereon, and then a TAG spot was detected under UV irradiation, then TAG fraction was collected.

For collected TAG fractions, the obtained fatty acid methyl esters were provided for gas chromatographic analysis by a method in a manner similar to described above. Table 4 shows the results.

TABLE 4

| | Fatty acid composition (% TFA) | | | | | | | (n = 3) TAG |
|---|---|---|---|---|---|---|---|---|
| | C10:0 | C12:0 | C14:0 | C16:1 | C16:0 | C18:n | C20:n | (mg/L) |
| NoTE | 2.1 ± 0.1 | 7.1 ± 3.0 | 15.2 ± 0.5 | 30.8 ± 1.0 | 17.1 ± 0.4 | 18.2 ± 0.9 | 9.4 ± 0.5 | 2822.9 ± 112.8 |
| NoTE + AT4295 | 3.5 ± 0.2 | 11.9 ± 0.4 | 18.2 ± 0.1 | 23.6 ± 0.0 | 16.6 ± 0.6 | 16.3 ± 0.3 | 9.8 ± 0.2 | 4286.6 ± 98.3 |

As shown in Table 4, it was confirmed that the ratios of medium-chain fatty acids (capric acid (C10:0), lauric acid (C12:0), and myristic acid (C14:0)) in the TAG, and the total amount of the TAG were significantly increased, by introducing the NoAT4295 gene into the strain into which the modified NoTE gene had been introduced.

As described above, the transformant in which productivities of the medium-chain fatty acids and the total fatty acids to be produced are improved can be prepared by enhancing the expression of the AT gene as specified in the present invention. Further, productivity of the medium-chain fatty acids and the total amount of the all fatty acids to be produced can be improved by culturing this transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-179167 filed in Japan on Sep. 11, 2015, which is entirely herein incorporated by reference.

What is claimed is:

1. A method of producing fatty acids or lipids containing the fatty acids, comprising the steps of:
    culturing a transformant under conditions suitable for production of fatty acids or lipids containing the fatty acids as components,
    producing fatty acids or lipids containing the fatty acids as components as a result of the culturing; and
    collecting the fatty acids or lipids containing the fatty acids,
    wherein the transformant is a host organism that has been transformed with a gene encoding a protein selected from the following protein (A) or (B):
    (A) a protein consisting of the amino acid sequence set forth in SEQ ID NO: 1; and
    (B) a protein consisting of an amino acid sequence having 90% or more identity with the amino acid sequence of the protein (A), and having acyltransferase activity;

wherein the gene is expressed during the culturing; and wherein productivity of the fatty acids or lipids containing the fatty acids as components is increased in the transformant as a result of the culturing, as compared to productivity of the host organism that has not been transformed with the gene.

2. The method of claim 1, wherein productivity of medium-chain fatty acids or lipids containing the medium-chain fatty acids as components is increased in the transformant as a result of the culturing, as compared to productivity of the host organism that has not been transformed with the gene.

3. The method of claim 1, wherein the total amount of all fatty acids produced by the transformant is increased as a result of the culturing, as compared to total amount of all fatty acids produced by the host organism that has not been transformed with the gene.

4. The method according to claim 1, wherein expression of a gene encoding an acyl-ACP thioesterase having substrate specificity to a medium-chain acyl-ACP is enhanced in the transformant, as compared to that of a transformant in which expression of the gene encoding the acyl-ACP thioesterase is not enhanced.

5. The method according to claim 1, wherein the transformant is a microalga.

6. The method according to claim 5, wherein the microalga is an alga belonging to the genus *Nannochloropsis*.

7. The method according to claim 1, wherein the lipids contain a fatty acid having 6 or more and 14 or less carbon atoms or an ester compound thereof.

8. A transformant, wherein the transformant is a host organism transformed with a gene encoding the following protein (A) or (B), wherein, as compared to the host organism that has not been transformed with the gene:

(a) expression of protein (A) or (B) is enhanced in the transformant;

and (b) at least either (i) the productivity of medium-chain fatty acids or lipids containing the medium-chain fatty acids as components is increased, or (ii) the total amount of all fatty acids produced in a cell of the transformant is increased;

wherein protein (A) is:

(A) a protein consisting of the amino acid sequence set forth in SEQ ID NO: 1;

and protein (B) is:

(B) a protein consisting of an amino acid sequence having 90% or more identity with the amino acid sequence of the protein (A), and having acyltransferase activity.

9. The transformant according to claim 8, wherein expression of a gene encoding an acyl-ACP thioesterase having substrate specificity to a medium-chain acyl-ACP is enhanced, as compared to that of a transformant in which expression of the gene encoding the acyl-ACP thioesterase is not enhanced.

10. The transformant according to claim 8, wherein the transformant is a microalga.

11. The transformant according to claim 10, wherein the microalga is an alga belonging to the genus *Nannochloropsis*.

12. The method according to claim 2, wherein expression of a gene encoding an acyl-ACP thioesterase having substrate specificity to a medium-chain acyl-ACP is enhanced in the transformant, as compared to that of a transformant in which expression of the gene encoding the acyl-ACP thioesterase is not enhanced.

13. The method according to claim 2, wherein the transformant is a microalga.

14. The method according to claim 13, wherein the microalga is an alga belonging to the genus *Nannochloropsis*.

15. The method according to claim 2, wherein the lipids contain a fatty acid having 6 or more and 14 or less carbon atoms or an ester compound thereof.

16. The method according to claim 3, wherein expression of a gene encoding an acyl-ACP thioesterase having substrate specificity to a medium-chain acyl-ACP is enhanced in the transformant, as compared to that of a transformant in which expression of the gene encoding the acyl-ACP thioesterase is not enhanced.

17. The method according to claim 3, wherein the transformant is a microalga.

18. The method according to claim 17, wherein the microalga is an alga belonging to the genus *Nannochloropsis*.

19. The method according to claim 3, wherein the lipids contain a a fatty acid having 6 or more and 14 or less carbon atoms or an ester compound thereof.

20. The method according to claim 1, wherein the gene encodes protein (A).

* * * * *